US010577569B2

(12) United States Patent
Benie et al.

(10) Patent No.: US 10,577,569 B2
(45) Date of Patent: Mar. 3, 2020

(54) POLYPEPTIDES SUITABLE FOR DETERGENT

(71) Applicant: NOVOZYMES A/S, Bagsvaerd (DK)

(72) Inventors: Astrid Benie, Vaerloese (DK); Jürgen C. F. Knötzel, København Ø (DK); Mikael Bauer, Malmo (SE); Lars L. H. Christensen, Alleroed (DK); Julie B. Rannes, Copenhagen O (DK); Jan Peter Skagerlind, Helsingborg (SE); Nan Gao, Beijing (CN)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

(21) Appl. No.: 15/569,167

(22) PCT Filed: Apr. 29, 2016

(86) PCT No.: PCT/EP2016/059669

§ 371 (c)(1),
(2) Date: Oct. 25, 2017

(87) PCT Pub. No.: WO2016/174234

PCT Pub. Date: Nov. 3, 2016

(65) Prior Publication Data

US 2018/0291314 A1 Oct. 11, 2018

(30) Foreign Application Priority Data

Apr. 29, 2015 (EP) .................................... 15165808

(51) Int. Cl.
*C12N 9/50* (2006.01)
*C11D 3/386* (2006.01)

(52) U.S. Cl.
CPC ................ *C11D 3/386* (2013.01); *C12N 9/50* (2013.01); *C12Y 304/21* (2013.01)

(58) Field of Classification Search
None
See application file for complete search history.

(56) References Cited

U.S. PATENT DOCUMENTS

| | | | | |
|---|---|---|---|---|
| 2012/0172280 A1* | 7/2012 | Knotzel | C11D 3/386 | 510/392 |
| 2012/0252106 A1* | 10/2012 | Knotzel | C11D 3/386 | 435/264 |
| 2013/0303424 A1* | 11/2013 | Scialla | C11D 1/62 | 510/220 |
| 2018/0291314 A1* | 10/2018 | Benie | C11D 3/386 | |

FOREIGN PATENT DOCUMENTS

| | | |
|---|---|---|
| WO | 2011/036263 A1 | 3/2011 |
| WO | 2011/036264 A1 | 3/2011 |

* cited by examiner

*Primary Examiner* — Richard C Ekstrom
(74) *Attorney, Agent, or Firm* — David Fazzolare

(57) ABSTRACT

The present invention relates to novel subtilase polypeptides exhibiting increased wash performance and/or improved wash performance and to compositions comprising such polypeptides. The polypeptides of the invention are suitable for use in e.g. cleaning or detergent compositions, such as laundry detergent compositions and dish wash compositions, including automatic dish wash compositions. The present invention also relates to isolated DNA sequences encoding the polypeptides, expression vectors, host cells, and methods for producing and using the polypeptides of the invention.

26 Claims, No Drawings

Specification includes a Sequence Listing.

POLYPEPTIDES SUITABLE FOR DETERGENT

CROSS-REFERENCE TO RELATED APPLICATIONS

This application is a 35 U.S.C. 371 national application of PCT/EP2016/059669 filed Apr. 29, 2016, which claims priority or the benefit under 35 U.S.C. 119 of European application no. 15165808.5 filed Apr. 29, 2015, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to novel polypeptides having protease activity. The polypeptides of the invention are suitable for use in e.g. cleaning or detergent compositions, such as laundry detergent compositions and dish wash compositions, including automatic dish wash compositions. The present invention also relates to detergent compositions, such as laundry and dish wash compositions comprising the polypeptides of the invention. The present invention also relates to isolated DNA sequences encoding the polypeptides, expression vectors, host cells, and methods for producing and using the polypeptides of the invention.

Description of the Related Art

In the detergent industry, enzymes have for many decades been implemented in washing formulations. Enzymes used in such formulations comprise proteases, lipases, amylases, cellulases, mannosidases as well as other enzymes or mixtures thereof. Commercially the most important enzymes are proteases.

An increasing number of commercially used proteases are protein engineered polypeptides of naturally occurring wild type proteases Everlase®, Relase®, Ovozyme®, Polarzyme®, Liquanase®, Liquanase Ultra® and Kannase® (Novozymes A/S), Purafast®, Purafect OXP®, FN3®, FN4® and Excellase® (Genencor International, Inc.).

However, various factors make further improvement of the enzymes used in e.g. detergents such as the proteases advantageous. The washing conditions such as temperature and pH changes over time and many stains are still difficult to completely remove under conventional washing conditions. Further, in wash conditions can result in inactivation of the enzymes (due to e.g. pH, temperature or chelation instability) resulting in loss of wash performance during the wash cycle. Thus despite the intensive research in protease development there remains a need for new and improved proteases that have improved properties such as increased stability and/or improved wash performance compared to the parent subtilase.

SUMMARY OF THE INVENTION

The present invention relates to polypeptides having protease activity, said polypeptide comprising an amino acid sequence selected from the group consisting of: SEQ ID NO 2, SEQ ID NO 4, SEQ ID NO 6, SEQ ID NO 8, SEQ ID NO 10, SEQ ID NO 12, SEQ ID NO 14, SEQ ID NO 16 and SEQ ID NO 18.

The polypeptides of the invention has improved stability and/or improved wash performance compared to a reference protease. The present invention further relates to polynucleotides encoding the polypeptides and methods for obtaining the polypeptides of the invention.

The invention further relates to detergent compositions such as:

A dish wash composition comprising:

a) at least 0.01 mg of active protease per gram of composition wherein the protease is selected from a polypeptide comprising SEQ ID NO 2, SEQ ID NO 4, SEQ ID NO 6, SEQ ID NO 8, SEQ ID NO 10, SEQ ID NO 12, SEQ ID NO 14, SEQ ID NO 16 or SEQ ID NO 18, b) at least one builder, and c) at least one bleach component.

In one aspect, the dish wash composition comprises a builder wherein the builder is selected among phosphates, sodium citrate builders, sodium carbonate, sodium silicate, sodium and zeolites, wherein the builder is added in an amount of about 0-65% by weight, preferably about 40-65% by weight, particularly about 20-65% by weight, particularly from 10% to 50% by weight.

The dish wash composition contains 0-50% by weight, such as about 5% to about 30%, of a detergent co-builder and/or the dish wash compositions is preferably phosphate free. According to one aspect of the invention the builder is selected from citric acid, methyl glycine-N,N-diacetic acid (MGDA) and/or glutamic-N,N-diacetic acid (GLDA) and mixtures thereof. According to one aspect of the invention the bleach component is selected from bleaching catalysts, photobleaches, bleach activators, sources of hydrogen peroxide such as sodium percarbonate, sodium perborates and hydrogen peroxide, preformed peracids and mixtures thereof. According to one aspect the bleach component is a peroxide such as percarbonate, persulfate, perphosphate, persilicate salts. In one aspect the bleaching component includes a percarbonate and bleach catalyst, preferably a manganese compound according to one aspect the bleach catalyst is 1,4,7-trimethyl-1,4,7-triazacyclononane or manganese (II) acetate tetrahydrate (MnTACN). In one aspect the dish wash composition comprising from 1-40 wt %, preferably from 0.5-30 wt %, of bleaching components, wherein the bleach components are a peroxide, preferably percabonate and a catalyst preferably a metal-containing bleach catalyst such as 1,4,7-trimethyl-1,4,7-triazacyclononane or manganese (II) acetate tetrahydrate (MnTACN).

One aspect of the invention relates to a granular detergent composition comprising:

a) at least 0.01 mg of active protease per gram of composition wherein the protease is selected from a polypeptide comprising SEQ ID NO 2, SEQ ID NO 4, SEQ ID NO 6, SEQ ID NO 8, SEQ ID NO 10, SEQ ID NO 12, SEQ ID NO 14, SEQ ID NO 16 or SEQ ID NO 18, b) 5 wt % to 50 wt % anionic surfactant c) 1 wt % to 8 wt % nonionic surfactant d) 5 wt % to 40 wt % builder such as carbonates, zeolites, phosphate builder, calcium sequestering builders or complexing agents In one aspect, the anion surfactant is one or more selected from linear alkylbenzenesulfonates (LAS) isomers of LAS, alcohol ether sulfate (AEO, AEOS) and sodium lauryl ether sulfate, sodium laureth sulfate (SLES). In one aspect the nonionic surfactant is selected from nonionic surfactants primary alcohol ethoxylates, such as Neodol 25-7 or Neodol 25-3, alkyl ester sulphates, especially C-9-15 alcohol ether-sulfates (AES), C12-15 primary alcohol ethoxylate such as alcohol ethoxylates (AE or AEO), sodium toluene sulfonate (STS) and sodium dodecyl sulfate (SDS). In one aspect the builder is a carbonates, zeolites builder. In one aspect of the invention the builder is selected from citric acid, methyl glycine-N,N-diacetic acid (MGDA) and/or glutamic-N,N-diacetic acid (GLDA) and mixtures thereof. In one aspect the granular detergent composition comprises a bleach component selected from a peroxide such as percarbonate, persulfate, perphosphate, persilicate salts.

In one aspect of the invention, the polypeptides selected from the group consisting of SEQ ID NO 2, SEQ ID NO 4, SEQ ID NO 6, SEQ ID NO 8, SEQ ID NO 10, SEQ ID NO 12, SEQ ID NO 14, SEQ ID NO 16 or SEQ ID NO 18 have improved wash performance on blood stains such as C-05 and CS-01 when compared to the polypeptide with SEQ ID NO 19.

The invention further relates to the use of a the dish wash or granular laundry composition as described above in a cleaning process, wherein the process is selected from a process of doing hard surface cleaning, such as dish wash, and a laundry process.

Definitions

Protease and Polypeptides Having Protease Activity

The term "protease" or "polypeptide having protease activity" is defined herein as an enzyme that hydrolyses peptide bonds. It includes any enzyme belonging to the EC 3.4 enzyme group (including each of the thirteen subclasses thereof). The EC number refers to Enzyme Nomenclature 1992 from NC-IUBMB, Academic Press, San Diego, Calif., including supplements 1-5 published in Eur. J. Biochem. 1994, 223, 1-5; Eur. J. Biochem. 1995, 232, 1-6; Eur. J. Biochem. 1996, 237, 1-5; Eur. J. Biochem. 1997, 250, 1-6; and Eur. J. Biochem. 1999, 264, 610-650; respectively.

The term "protease activity" means a proteolytic activity (EC 3.4). Proteases of the invention are endopeptidases (EC 3.4.21). There are several protease activity types: The three main activity types are: trypsin-like where there is cleavage of amide substrates following Arg or Lys at P1, chymotrypsin-like where cleavage occurs following one of the hydrophobic amino acids at P1, and elastase-like with cleavage following an Ala at P1. For purposes of the present invention, protease activity is determined according to the procedure described in "Materials and Methods" below. The polypeptides of the present invention have at least 20%, e.g., at least 40%, at least 50%, at least 60%, at least 70%, at least 80%, at least 90%, at least 95%, and at least 100% of the protease activity of the polypeptide of SEQ ID NO 19.

The term "reference protease" or "reference polypeptide" means a protease or polypeptide with protease activity these terms are used interchangeably in the application. The reference protease may be any prior art protease having at least one property which is improved by the polypeptide of the invention. Such properties could be wash performance and/or stability in detergent. The reference protease may be a naturally occurring (wild-type) polypeptide or a variant thereof. In a particular embodiment the reference protease is a protease with at least 60% identity, such as at least 65%, at least 70%, at least 75%, at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% identity to a polypeptide with the polypeptide with SEQ ID NO 19. SEQ ID NO 19 is the subtilisin 309 protease also known as Savinase, which is well known for its wash performance in detergent and which is widely used in detergents today.

The term "wild-type protease" means a protease expressed by a naturally occurring organism, such as a bacterium, archaea, yeast, fungus, plant or animal found in nature. An example of a wild-type subtilase is subtilisin 309 i.e. the polypeptide with the amino acid sequence SEQ ID NO 19.

The relatedness between two amino acid sequences or between two nucleotide sequences is described by the parameter "sequence identity". For purposes of the present invention, the sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labled "longest identity" (obtained using the –nobrief option) is used as the percent identity and is calculated as follows:

$$(\text{Identical Residues} \times 100)/(\text{Length of Alignment} - \text{Total Number of Gaps in Alignment})$$

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labled "longest identity" (obtained using the –nobrief option) is used as the percent identity and is calculated as follows:

$$(\text{Identical Deoxyribonucleotides} \times 100)/(\text{Length of Alignment} - \text{Total Number of Gaps in Alignment})$$

The term "variant" means a polypeptide having protease activity comprising an alteration, i.e., a substitution, insertion, and/or deletion, at one or more (e.g., several) positions compared to the precursor polypeptide or starting peptide. E.g. a variant of SEQ ID NO 19 is a polypeptide which has at least one an alteration, i.e., a substitution, insertion, and/or deletion, at one or more (e.g., several) positions compared SEQ ID NO 19. A substitution means replacement of the amino acid occupying a position with a different amino acid; a deletion means removal of the amino acid occupying a position; and an insertion means adding one or more (e.g. several) amino acids, e.g. 1, 2, 3, 4 or 5 amino acids adjacent to and immediately following the amino acid occupying a position.

The term "mature polypeptide" means a polypeptide in its final form following translation and any post-translational modifications, such as N-terminal processing, C-terminal truncation, glycosylation, phosphorylation, etc. It is known in the art that a host cell may produce a mixture of two of more different mature polypeptides (i.e., with a different C-terminal and/or N-terminal amino acid) expressed by the same polynucleotide.

The term "mature polypeptide coding sequence" means a polynucleotide that encodes a mature polypeptide having protease activity.

The term "substantially pure polypeptide" means a preparation that contains at most 10%, at most 8%, at most 6%, at most 5%, at most 4%, at most 3%, at most 2%, at most 1%, and at most 0.5% by weight of other polypeptide material with which it is natively or recombinantly associated. Preferably, the polypeptides of the invention are at least 92% pure, e.g., at least 94% pure, at least 95% pure, at least 96% pure, at least 97% pure, at least 98% pure, at least 99%, at least 99.5% pure, and 100% pure by weight of the total polypeptide material present in the preparation. The polypeptides of the present invention are preferably in a substantially pure form. This can be accomplished, for example, by preparing the polypeptides by well-known recombinant methods or by classical purification methods.

The term "substantially pure polynucleotide" means a polynucleotide preparation free of other extraneous or unwanted nucleotides and in a form suitable for use within genetically engineered polypeptide production systems. Thus, a substantially pure polynucleotide contains at most 10%, at most 8%, at most 6%, at most 5%, at most 4%, at most 3%, at most 2%, at most 1%, and at most 0.5% by weight of other polynucleotide material with which it is natively or recombinantly associated. A substantially pure polynucleotide may, however, include naturally occurring 5'- and 3'-untranslated regions, such as promoters and terminators. It is preferred that the substantially pure polynucleotide is at least 90% pure, e.g., at least 92% pure, at least 94% pure, at least 95% pure, at least 96% pure, at least 97% pure, at least 98% pure, at least 99% pure, and at least 99.5% pure by weight. The polynucleotides of the present invention are preferably in a substantially pure form.

The term "isolated" means a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Detergents

The term "detergent composition" includes, unless otherwise indicated, all forms of detergent compositions such as gel, granulate, liquid, paste, powder, spray or tablet compositions including heavy-duty liquids (HDL), fine-fabric liquid detergents, liquid and/or solid laundry detergents and fine fabric detergents; hard surface cleaning formulations for e.g. glass, wood, ceramic and metal counter tops and windows; carpet cleaners; oven cleaners; fabric fresheners; fabric softeners; textile and laundry pre-spotters, as well as dish wash detergents such as hand dishwashing agents, light duty dishwashing agents, machine dishwashing agents such as automatic dish wash (ADW); all-purpose or heavy-duty washing agents, liquid, gel or paste-form all-purpose washing agents, liquid cleaning and disinfecting agents, including antibacterial hand-wash types, cleaning bars, mouthwashes, denture cleaners, car or carpet shampoos, bathroom cleaners; hair shampoos and hair-rinses; shower gels, foam baths; metal cleaners; as well as cleaning auxiliaries such as bleach additives and "stain-stick" or pre-treat types.

In addition to containing a subtilase polypeotide of the invention, the detergent formulation may contain one or more additional enzymes (such as proteases, amylases, lipases, cutinases, cellulases, endoglucanases, xyloglucanases, pectinases, pectin lyases, xanthanases, peroxidaes, haloperoxygenases, catalases and mannanases, or any mixture thereof), and/or components such as surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti-corrosion agents, enzyme inhibitors or stabilizers, enzyme activators, transferase(s), hydrolytic enzymes, oxido reductases, bluing agents and fluorescent dyes, antioxidants, and solubilizers.

The term "detergent component" is defined herein to mean the types of chemicals which can be used in detergent compositions. Examples of detergent components are surfactants, hydrotropes, builders, co-builders, chelators or chelating agents, bleaching system or bleach components, polymers, fabric hueing agents, fabric conditioners, foam boosters, suds suppressors, dispersants, dye transfer inhibitors, fluorescent whitening agents, perfume, optical brighteners, bactericides, fungicides, soil suspending agents, soil release polymers, anti-redeposition agents, enzyme inhibitors or stabilizers, enzyme activators, antioxidants, and solubilizers. The detergent composition may comprise one or more of any type of detergent component.

The term "dish wash" refers to all forms of washing dishes, e.g. by hand or automatic dish wash (ADW). Washing dishes includes, but is not limited to, the cleaning of all forms of crockery such as plates, cups, glasses, bowls, all forms of cutlery such as spoons, knives, forks and serving utensils as well as ceramics, plastics such as melamine, metals, china, glass and acrylics.

The term "dish washing composition" refers to compositions intended for cleaning dishes, table ware, pots, pans, cutlery and all forms of compositions for cleaning hard surfaces areas in kitchens. The present invention is not restricted to any particular type of dish wash composition or any particular detergent.

The term "Hard surface cleaning" is defined herein as cleaning of hard surfaces wherein hard surfaces may include floors, tables, walls, roofs etc. as well as surfaces of hard objects such as cars (car wash) and dishes (dish wash). Dish washing includes but are not limited to cleaning of plates, cups, glasses, bowls, cutlery such as spoons, knives, forks, serving utensils, ceramics, plastics, metals, china, glass and acrylics.

The term "improved property" means a characteristic associated with a polypeptide that is improved compared to a reference protease the reference protease is in the context of the present application the polypeptide with the amino acid sequence SEQ ID NO 19. Such improved properties include, but are not limited to, chelator stability, wash performance, protease activity, thermal activity profile, thermostability, pH activity profile, pH stability, substrate/cofactor specificity, improved surface properties, substrate specificity, product specificity, increased stability or solubility in the presence of pretreated biomass, improved stability under storage conditions (storage stability), improved in wash stability and chemical stability. Preferred embodiments are improved wash performance and improved stability, preferably improved in wash stability.

The term "improved stability" covers all forms of improved stability, such as improved storage stability, improved pH stability, improved thermostability, improved chelator stability, improved chemical stability and improved in wash stability.

The term "improved wash performance" is defined herein as a polypeptide displaying an alteration of the wash performance relative to a reference protease such as a protease with SEQ ID NO 19, e.g. by increased stain removal. The term "wash performance" includes wash performance in dish wash but also in laundry. The wash performance may be determined by calculating the so-called intensity value (Int) as defined in the Automatic Mechanical Stress Assay (AMSA) for Automatic Dish Wash in the Materials and Methods section herein.

The term "laundering" relates to both household laundering and industrial laundering and means the process of treating textiles and/or fabrics with a solution containing a detergent composition of the present invention. The laundering process can for example be carried out using e.g. a household or an industrial washing machine or can be carried out by hand.

The term "stability" includes storage stability and stability during use, e.g. during a wash process (in wash stability) and reflects the stability of the polypeptides according to the invention as a function of time e.g. how much activity is retained when the polypeptide is kept in solution, in particular in a detergent solution. The stability is influenced by many factors e.g. pH, temperature, detergent composition e.g. amount of builder, surfactants etc.

The term "textile" means any textile material including yarns, yarn intermediates, fibers, non-woven materials, natural materials, synthetic materials, and any other textile material, fabrics made of these materials and products made from fabrics (e.g., garments and other articles). The textile or fabric may be in the form of knits, wovens, denims, non-wovens, felts, yarns, and towelling. The textile may be cellulose based such as natural cellulosics, including cotton, flax/linen, jute, ramie, sisal or coir or manmade cellulosics (e.g. originating from wood pulp) including viscose/rayon, cellulose acetate fibers (tricell), lyocell or blends thereof. The textile or fabric may also be non-cellulose based such as natural polyamides including wool, camel, cashmere, mohair, rabbit and silk or synthetic polymers such as nylon, aramid, polyester, acrylic, polypropylene and spandex/elastane, or blends thereof as well as blends of cellulose based and non-cellulose based fibers. Examples of blends are blends of cotton and/or rayon/viscose with one or more companion material such as wool, synthetic fiber (e.g. polyamide fiber, acrylic fiber, polyester fiber, polyvinyl chloride fiber, polyurethane fiber, polyurea fiber, aramid fiber), and/or cellulose-containing fiber (e.g. rayon/viscose, ramie, flax/linen, jute, cellulose acetate fiber, lyocell). Fabric may be conventional washable laundry, for example stained household laundry. When the term fabric or garment is used it is intended to include the broader term textiles as well.

The term "wash performance" is used as an enzyme's ability to remove stains present on the object to be cleaned during e.g. wash, such as laundry or hard surface cleaning. The improvement in the wash performance may be quantified by calculating the so-called intensity value (Int) also defined in AMSA assay, as described in Materials and Methods section.

Delta remission value (ARem): The terms "Delta remission" or "Delta remission value" are defined herein as the result of a reflectance or remission measurement at a certain wavelength which typically is 460 nm. The swatch is measured with one swatch of similar colour as background, preferably a swatch from a repetition wash. A swatch representing each swatch type is measured before the wash. The Delta remission is the remission value of the washed swatch minus the remission value of the unwashed swatch.

One way of measuring the wash performance is the Delta enzyme performance value (ARem enzyme value): The term "Delta enzyme remission value" is defined herein as the result of a reflectance or remission measurement at 460 nm. The swatch is measured with one swatch of similar colour as background, preferably a swatch from a repetition wash. A swatch representing each swatch type is measured before wash. The Delta enzyme remission is the remission value of the swatch washed in detergent with an enzyme present minus the remission value of a similar swatch washed in a detergent without enzyme present.

DETAILED DESCRIPTION OF THE INVENTION

The present invention relates to a polypeptide having protease activity, said polypeptide comprising an amino acid sequence having at least 60% sequence identity to a polypeptide sequence selected from the group consisting of: SEQ ID NO 19.

One aspect of the invention relates to a polypeptide having protease activity, said polypeptide comprising an amino acid sequence having at least 60%, such as at least 65%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity to the amino acid sequence with SEQ ID NO 19.

The invention further relates to a polypeptide having protease activity, said polypeptide comprising an amino acid sequence selected from the group consisting of: SEQ ID NO 2, SEQ ID NO 4, SEQ ID NO 6, SEQ ID NO 8, SEQ ID NO 10, SEQ ID NO 12, SEQ ID NO 14, SEQ ID NO 16 and SEQ ID NO 18.

In one embodiment, the invention relates to a polypeptide having protease activity, wherein the polypeptide comprises or consists of the amino acid sequence with SEQ ID NO 2.

In one embodiment, the invention relates to a polypeptide having protease activity, wherein the polypeptide comprises or consists of the amino acid sequence with SEQ ID NO 4.

In one embodiment, the invention relates to a polypeptide having protease activity, wherein the polypeptide comprises or consists of the amino acid sequence with SEQ ID NO 6.

In one embodiment, the invention relates to a polypeptide having protease activity, wherein the polypeptide comprises or consists of the amino acid sequence with SEQ ID NO 8.

In one embodiment, the invention relates to a polypeptide having protease activity, wherein the polypeptide comprises or consists of the amino acid sequence with SEQ ID NO 10.

In one embodiment, the invention relates to a polypeptide having protease activity, wherein the polypeptide comprises or consists of the amino acid sequence with SEQ ID NO 12.

In one embodiment, the invention relates to a polypeptide having protease activity, wherein the polypeptide comprises or consists of the amino acid sequence with SEQ ID NO 14.

In one embodiment, the invention relates to a polypeptide having protease activity, wherein the polypeptide comprises or consists of the amino acid sequence with SEQ ID NO 16.

In one embodiment, the invention relates to a polypeptide having protease activity, wherein the polypeptide comprises or consists of the amino acid sequence with SEQ ID NO 18.

In a preferred embodiment, the polypeptides of the invention have improved wash performance compared to a reference protease e.g. compared to SEQ ID NO 19. In a preferred embodiment, the polypeptides of the invention have improved wash performance and/or improved detergent stability compared to a reference protease e.g. compared to SEQ ID NO 19.

The invention further relates to a polypeptide having protease activity, wherein the polypeptide comprise an amino acid sequence selected from the group consisting of: SEQ ID NO 2, SEQ ID NO 4, SEQ ID NO 6, SEQ ID NO 8, SEQ ID NO 10, SEQ ID NO 12, SEQ ID NO 14, SEQ ID NO 16 and SEQ ID NO 18 wherein said polypeptide has improved wash performance compared to the polypeptide with SEQ ID NO 19.

In one embodiment, the invention relates to a polypeptide having protease activity, wherein the polypeptide comprises or consists of the amino acid sequence with SEQ ID NO 2, and wherein the polypeptide has improved wash performance compared to the polypeptide with SEQ ID NO 19.

In one embodiment, the invention relates to a polypeptide having protease activity, wherein the polypeptide comprises or consists of the amino acid sequence with SEQ ID NO 4, and wherein the polypeptide has improved wash performance compared to the polypeptide with SEQ ID NO 19.

In one embodiment, the invention relates to a polypeptide having protease activity, wherein the polypeptide comprises or consists of the amino acid sequence with SEQ ID NO 6, and wherein the polypeptide has improved wash performance compared to the polypeptide with SEQ ID NO 19.

In one embodiment, the invention relates to a polypeptide having protease activity, wherein the polypeptide comprises or consists of the amino acid sequence with SEQ ID NO 8, and wherein the polypeptide has improved wash performance compared to the polypeptide with SEQ ID NO 19.

In one embodiment, the invention relates to a polypeptide having protease activity, wherein the polypeptide comprises or consists of the amino acid sequence with SEQ ID NO 10, and wherein the polypeptide has improved wash performance compared to the polypeptide with SEQ ID NO 19.

In one embodiment, the invention relates to a polypeptide having protease activity, wherein the polypeptide comprises or consists of the amino acid sequence with SEQ ID NO 12, and wherein the polypeptide has improved wash performance compared to the polypeptide with SEQ ID NO 19.

In one embodiment, the invention relates to a polypeptide having protease activity, wherein the polypeptide comprises or consists of the amino acid sequence with SEQ ID NO 14, and wherein the polypeptide has improved wash performance compared to the polypeptide with SEQ ID NO 19.

In one embodiment, the invention relates to a polypeptide having protease activity, wherein the polypeptide comprises or consists of the amino acid sequence with SEQ ID NO 16, and wherein the polypeptide has improved wash performance compared to the polypeptide with SEQ ID NO 19.

In one embodiment, the invention relates to a polypeptide having protease activity, wherein the polypeptide comprises or consists of the amino acid sequence with SEQ ID NO 18, and wherein the polypeptide has improved wash performance compared to the polypeptide with SEQ ID NO 19.

In one embodiment, the polypeptides comprising SEQ ID NO 2, SEQ ID NO 4, SEQ ID NO 6, SEQ ID NO 8, SEQ ID NO 10, SEQ ID NO 12, SEQ ID NO 14, SEQ ID NO 16 or SEQ ID NO 18 have improved performance, in particular improved in wash performance, compared to a reference polypeptide such as the polypeptide with SEQ ID NO 19. In a preferred embodiment, the polypeptides comprising SEQ ID NO 2, SEQ ID NO 4, SEQ ID NO 6, SEQ ID NO 8, SEQ ID NO 10, SEQ ID NO 12, SEQ ID NO 14, SEQ ID NO 16 or SEQ ID NO 18 have improved stability, in particular improved in wash stability, and on par or improved wash performance compared to a reference polypeptide such as the polypeptide with SEQ ID NO 19.

In one embodiment, the invention relates to a polypeptide having protease activity, wherein said polypeptide comprises the amino acid sequence selected from the group consisting of SEQ ID NO 2, SEQ ID NO 4, SEQ ID NO 6, SEQ ID NO 8, SEQ ID NO 10, SEQ ID NO 12, SEQ ID NO 14, SEQ ID NO 16 and SEQ ID NO 18 and wherein the polypeptide sequence has at least 60%, such as at least 65%, at least 70%, at least 75%, at least 80%, at least 85%, at least 90%, at least 91%, at least 92%, at least 93%, at least 94%, at least 95%, at least 96%, at least 97%, at least 98% or at least 99% but less than 100% sequence identity to the amino acid sequence of SEQ ID NO 19.

In an embodiment, the polypeptide comprises the amino acid sequence selected from the group consisting of SEQ ID NO 2, SEQ ID NO 4, SEQ ID NO 6, SEQ ID NO 8, SEQ ID NO 10, SEQ ID NO 12, SEQ ID NO 14, SEQ ID NO 16 and SEQ ID NO 18 has at least 65% but less than 100% sequence identity to the mature polypeptide of SEQ ID NO 19. In an embodiment, the polypeptide has at least 70% but less than 100% sequence identity to the mature polypeptide of the SEQ ID NO 19. In an embodiment, the polypeptide has at least 75% but less than 100% sequence identity to the mature polypeptide of the SEQ ID NO 19. In an embodiment, the polypeptide has at least 80% but less than 100% sequence identity to the mature polypeptide of the SEQ ID NO 19. In an embodiment, the polypeptide has at least 85% but less than 100% sequence identity to the mature polypeptide of the SEQ ID NO 19. In an embodiment, the polypeptide has at least 90% but less than 100% sequence identity to the mature polypeptide of the SEQ ID NO 19. In an embodiment, the polypeptide has at least 93% but less than 100% sequence identity to the mature polypeptide of the SEQ ID NO 19. In an embodiment, the polypeptide has at least 95% but less than 100% sequence identity to the mature polypeptide of the SEQ ID NO 19. In an embodiment, the polypeptide has at least 96% but less than 100% sequence identity to the mature polypeptide of the SEQ ID NO 19. In an embodiment, the polypeptide has at least 97% but less than 100% sequence identity to the mature polypeptide of the SEQ ID NO 19. In an embodiment, the polypeptide has at least 98% but less than 100% sequence identity to the mature polypeptide of the SEQ ID NO 19.

In one aspect, the total number of alterations in the polypeptides of the invention compared to the SEQ ID NO 19 is between 5 and 30, preferably between 8 and 20, more preferably between 8 and 15, even more preferably between 8 and 10, most preferably between 3 and 8 alterations. In another aspect, total number of alterations compared to the polypeptide with SEQ ID NO 19 is 3, 4, 5, 6, 7, 8, 9, 10, 11, 12, 13, 14, 15, 16, 17, 18, 19, 20, 21, 22, 23, 24, 25, 26, 27, 28, 29 or 30 alterations.

In one embodiment, the polypeptide of the invention has improved performance, in particular improved wash performance, compared to the mature polypeptide of the SEQ ID NO 19. In a preferred embodiment, the polypeptides of the invention have improved performance, in particular improved wash performance, and on par or improved stability compared to the mature polypeptide of the SEQ ID NO 19.

In one embodiment, the polypeptides comprise the amino acid sequences SEQ ID NO 2, SEQ ID NO 4, SEQ ID NO 6, SEQ ID NO 8, SEQ ID NO 10, SEQ ID NO 12, SEQ ID NO 14, SEQ ID NO 16 or SEQ ID NO 18, wherein the polypeptides comprise an alteration at one or more of the positions selected from the group consisting of 3, 4, 9, 15, 24, 42, 52, 59, 60, 66, 74, 76, 85, 96, 97, 99, 100, 101, 102, 103, 116, 118, 125, 126, 127, 128, 129, 135, 150, 160, 161, 164, 182, 188, 193, 199, 200, 203, 211, 212, 216, 239, 255 and 256 when compared to SEQ ID NO 19, wherein the polypeptide has at least 60% but less than 100% sequence identity to the amino acid sequence SEQ ID NO 19.

In one embodiment, the polypeptides comprising the amino acid sequences SEQ ID NO 2, SEQ ID NO 4, SEQ ID NO 6, SEQ ID NO 8, SEQ ID NO 10, SEQ ID NO 12, SEQ ID NO 14, SEQ ID NO 16, SEQ ID NO 18 or SEQ ID NO 19 wherein the polypeptides comprises one or more of the alterations selected from the group consisting of S3V/T, V41, S9R, A15T, N42D/R/K, G59E/D, N60D/E, V66A, N74D, S76N, S85N/E, A96E/D, S97D/E, S99G/E/N/H, G100, S101A, V102I, S103, G116V, H118N/D, G125, S126L/FN, P127Q/N/L, S128A, P129T, P129*, Q135H, S160G/K, Y161A, R164S/L, S182T, A188P, V193M, V199I, Q200E, Y203W, L211D/Q, N212D/S, M216A/S, Q239R, N255D/E and L256Y/E/D when compared to SEQ ID NO 19, wherein the polypeptide has at least 60% but less than 100% sequence identity to the amino acid sequence SEQ ID NO 19.

In one embodiment of the invention, the polypeptides consist of the amino acid sequences SEQ ID NO 2, SEQ ID NO 4, SEQ ID NO 6, SEQ ID NO 8, SEQ ID NO 10, SEQ ID NO 12, SEQ ID NO 14, SEQ ID NO 16 or SEQ ID NO 18. In one embodiment, the polypeptides have improved wash performance and/or improved stability, compared to a reference polypeptide or compared to SEQ ID NO 19.

The polypeptides of the invention may further comprise additional amino acid changes in addition to those listed above such amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for protease activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. For Savinase (SEQ ID NO: 4) the catalytic triad comprising the amino acids S221, H64, and D32 (BPN' numbering) is essential for protease activity of the enzyme.

The polypeptides of the invention may consist of 150 to 350, e.g., 175 to 330, 200 to 310, 220 to 300, 240 to 290, 260 to 280 or 269 amino acids.

The polypeptides can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, Proc. Natl. Acad. Sci. USA 76: 4949-4955; and Barton et al., 1990, Nucleic Acids Res. 18: 7349-4966.

Site-directed mutagenesis can also be accomplished in vivo by methods known in the art. See, e.g., U.S. Patent Application Publication No. 2004/0171154; Storici et al., 2001, Nature Biotechnol. 19: 773-776; Kren et al., 1998, Nat. Med. 4: 285-290; and Calissano and Macino, 1996, Fungal Genet. Newslett. 43: 15-16.

Any site-directed mutagenesis procedure can be used in the present invention. There are many commercial kits available that can be used to prepare polypeptides.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, Nature 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241:

53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochemistry 30: 10832-10837; U.S. Pat. No. 5,223,409; WO 92/06204) and region-directed mutagenesis (Derbyshire et al., 1986, Gene 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, Nature Biotechnology 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide sub-sequences may then be shuffled.

In an embodiment, the polypeptide selected from the group consisting of the amino acid sequences SEQ ID NO 2, SEQ ID NO 4, SEQ ID NO 6, SEQ ID NO 8, SEQ ID NO 10, SEQ ID NO 12, SEQ ID NO 14, SEQ ID NO 16 and SEQ ID NO 18 has improved stability, in particular improved in wash stability, compared the a reference polypeptide such as the polypeptide with SEQ ID NO 19 wherein in wash stability is measured using the 'in wash stability assay' as described in the Materials and Methods section herein.

In an embodiment, the polypeptide selected from the group consisting of the amino acid sequences SEQ ID NO 2, SEQ ID NO 4, SEQ ID NO 6, SEQ ID NO 8, SEQ ID NO 10, SEQ ID NO 12, SEQ ID NO 14, SEQ ID NO 16 and SEQ ID NO 18 has improved wash performance compared the a reference polypeptide such as the polypeptide with SEQ ID NO 19 wherein in wash performance is measured using the Automatic Mechanical Stress Assay (AMSA) for Automatic Dish Wash as described in the Materials and Methods section herein. In an embodiment, the polypeptide selected from the group consisting of the amino acid sequences SEQ ID NO 2, SEQ ID NO 4, SEQ ID NO 6, SEQ ID NO 8, SEQ ID NO 10, SEQ ID NO 12, SEQ ID NO 14, SEQ ID NO 16 and SEQ ID NO 18 has improved stability, in particular improved in wash stability and improved wash performance compared to the polypeptide of SEQ ID NO 19, wherein in wash stability is measured using the 'In Wash Stability Assay' and wash performance is measured using the Automatic Mechanical Stress Assay (AMSA) for Automatic Dish Wash as described in the Materials and Methods section herein.

The invention further relates to detergent compositions such as dish wash and laundry compositions and the use of such compositions in cleaning processes such as hard surface cleaning and laundry.

One embodiment of the invention relates to a dish wash composition comprising:

a) at least 0.01 mg of active protease per gram of composition, wherein the protease is selected from a polypeptide comprising SEQ ID NO 2, SEQ ID NO 4, SEQ ID NO 6, SEQ ID NO 8, SEQ ID NO 10, SEQ ID NO 12, SEQ ID NO 14, SEQ ID NO 16 or SEQ ID NO 18, b) at least one builder, and c) at least one bleach component.

The builder is preferably selected among phosphates, sodium citrate builders, sodium carbonate, sodium silicate, sodium aluminosilicate (zeolite). Suitable builders are alkali metal or ammonium phosphates, polyphosphates, phosphonates, polyphosphonates, carbonates, bicarbonates, borates, citrates, and polycarboxylates. Citrate builders, e.g., citric acid and soluble salts thereof (particularly sodium salt), are polycarboxylate builders. Citrates can be used in combination with zeolite, silicates like the BRITESIL types, and/or layered silicate builders. The builder is preferably added in an amount of about 0-65% by weight, such as about 5% to about 50% by weight. In a dish wash detergent, the level of builder is typically about 40-65% by weight, particularly about 50-65% by weight, particularly from 20% to 50% by weight. The builder and/or co-builder may particularly be a chelating agent that forms water-soluble complexes with Ca and Mg. Any builder and/or co-builder known in the art for use in cleaning detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), and (carboxymethyl) inulin (CMI), and combinations thereof. Further non-limiting examples of builders include citrate, chelators such as aminocarboxylates, aminopolycarboxylates and phosphonates, and alkyl- or alkenylsuccinic acid. Additional specific examples include 2,2',2"-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycine-N,N-diacetic acid (MGDA), glutamic acid-N,N-diacetic acid (GLDA), 1-hydroxyethane-1,1-diphosphonic acid, N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(sulfomethyl)aspartic acid (SMAS), N-(2-sulfoethyl)-aspartic acid (SEAS), N-(sulfomethylglutamic acid (SMGL), N-(2-sulfoethyl)-glutamic acid (SEGL), N-methyliminodiacetic acid (MIDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and N"-(2-hydroxyethypethylenediamine-N,N,N'-triacetic acid (HEDTA), diethanolglycine (DEG), and combinations and salts thereof.

Phosphonates suitable for use herein include 1-hydroxyethane-1,1-diphosphonic acid (HEDP), ethylenediaminetetrakis(methylenephosphonic acid) (EDTMPA), diethylenetriaminepentakis(methylenephosphonic acid) (DTMPA or DTPMPA or DTPMP), nitrilotris(methylenephosphonic acid) (ATMP or NTMP), 2-phosphonobutane-1,2,4-tricarboxylic acid (PBTC), hexamethylenediaminetetrakis(methylenephosphonic acid) (HDTMP)

The dish wash composition may also contain 0-50% by weight, such as about 5% to about 30%, of a detergent co-builder.

The detergent composition may include a co-builder alone, or in combination with a builder, for example a zeolite builder. Non-limiting examples of co-builders include homopolymers of polyacrylates or copolymers thereof, such as poly(acrylic acid) (PAA) or copoly(acrylic acid/maleic acid) (PAA/PMA) or polyaspartic acid.

Further exemplary builders and/or co-builders are described in, e.g., WO 09/102854, U.S. Pat. No. 5,977,053

In one preferred embodiment, the builder is a non-phosphorus based builder such as citric acid and/or methylglycine-N,N-diacetic acid (MGDA) and/or glutamic-N,N-diacetic acid (GLDA) and/or salts thereof.

One embodiment relates a dish washing composition comprising at least one protease wherein the protease is selected from a polypeptide comprising SEQ ID NO 2, SEQ ID NO 4, SEQ ID NO 6, SEQ ID NO 8, SEQ ID NO 10, SEQ ID NO 12, SEQ ID NO 14, SEQ ID NO 16 or SEQ ID NO 18, and a non-phosphate builder selected from citric acid, methyl glycine-N,N-diacetic acid (MGDA) and/or glutamic-N,N-diacetic acid (GLDA) and mixtures thereof.

According to one embodiment, the dish wash composition is an automatic dish wash composition (ADW) comprising:

a) at least 0.01 mg of active protease per gram of composition wherein the protease is selected from a polypeptide comprising SEQ ID NO 2, SEQ ID NO 4, SEQ ID NO 6, SEQ ID NO 8, SEQ ID NO 10, SEQ ID NO 12, SEQ ID NO 14, SEQ ID NO 16 or SEQ ID NO 18, and b) 10-50 wt % builder selected from citric acid, methylglycine-N,N-diacetic acid (MGDA) and/or glutamic acid-N,N-diacetic acid (GLDA) and mixtures thereof, and c) at least one bleach component.

According to one embodiment, the dish wash composition is an automatic dish wash composition (ADW) comprising:

a) at least 0.01 mg of active protease per gram of composition wherein the protease is selected from a polypeptide comprising SEQ ID NO 2, and b) 10-50 wt % builder selected from citric acid, methyl glycine-N,N-diacetic acid (MGDA) and/or glutamic-N,N-diacetic acid (GLDA) and mixtures thereof, and c) at least one bleach component.

According to one embodiment, the dish wash composition is an automatic dish wash composition (ADW) comprising:

a) at least 0.01 mg of active protease per gram of composition wherein the protease is selected from a polypeptide comprising SEQ ID NO 4, and b) 10-50 wt % builder selected from citric acid, methyl glycine-N,N-diacetic acid (MGDA) and/or glutamic-N,N-diacetic acid (GLDA) and mixtures thereof, and c) at least one bleach component.

According to one embodiment, the dish wash composition is an automatic dish wash composition (ADW) comprising:

a) at least 0.01 mg of active protease per gram of composition wherein the protease is selected from a polypeptide comprising SEQ ID NO 6, and b) 10-50 wt % builder selected from citric acid, methyl glycine-N,N-diacetic acid (MGDA) and/or glutamic-N,N-diacetic acid (GLDA) and mixtures thereof, and c) at least one bleach component.

According to one embodiment, the dish wash composition is an automatic dish wash composition (ADW) comprising:

a) at least 0.01 mg of active protease per gram of composition wherein the protease is selected from a polypeptide comprising SEQ ID NO 8, and b) 10-50 wt % builder selected from citric acid, methyl glycine-N,N-diacetic acid (MGDA) and/or glutamic-N,N-diacetic acid (GLDA) and mixtures thereof, and c) at least one bleach component.

According to one embodiment, the dish wash composition is an automatic dish wash composition (ADW) comprising:

a) at least 0.01 mg of active protease per gram of composition wherein the protease is selected from a polypeptide comprising SEQ ID NO 10, and b) 10-50 wt % builder selected from citric acid, methyl glycine-N,N-diacetic acid (MGDA) and/or glutamic-N,N-diacetic acid (GLDA) and mixtures thereof, and c) at least one bleach component.

According to one embodiment, the dish wash composition is an automatic dish wash composition (ADW) comprising:

a) at least 0.01 mg of active protease per gram of composition wherein the protease is selected from a polypeptide comprising SEQ ID NO 12, and b) 10-50 wt % builder selected from citric acid, methyl glycine-N,N-diacetic acid (MGDA) and/or glutamic-N,N-diacetic acid (GLDA) and mixtures thereof, and c) at least one bleach component.

According to one embodiment, the dish wash composition is an automatic dish wash composition (ADW) comprising:

a) at least 0.01 mg of active protease per gram of composition wherein the protease is selected from a polypeptide comprising SEQ ID NO 14, and b) 10-50 wt % builder selected from citric acid, methyl glycine-N,N-diacetic acid (MGDA) and/or glutamic-N,N-diacetic acid (GLDA) and mixtures thereof, and c) at least one bleach component.

According to one embodiment, the dish wash composition is an automatic dish wash composition (ADW) comprising:

a) at least 0.01 mg of active protease per gram of composition wherein the protease is selected from a polypeptide comprising SEQ ID NO 16, and b) 10-50 wt % builder selected from citric acid, methyl glycine-N,N-diacetic acid (MGDA) and/or glutamic-N,N-diacetic acid (GLDA) and mixtures thereof, and c) at least one bleach component.

According to one embodiment, the dish wash composition is an automatic dish wash composition (ADW) comprising:

a) at least 0.01 mg of active protease per gram of composition wherein the protease is selected from a polypeptide comprising SEQ ID NO 18, and b) 10-50 wt % builder selected from citric acid, methyl glycine-N,N-diacetic acid (MGDA) and/or glutamic-N,N-diacetic acid (GLDA) and mixtures thereof, and c) at least one bleach component.

One embodiment the dish wash composition is an automatic dish wash composition (ADW) comprising:

a) at least 0.01 mg of active protease per gram of composition wherein the protease is selected from a polypeptide comprising SEQ ID NO 2, SEQ ID NO 4, SEQ ID NO 6, SEQ ID NO 8, SEQ ID NO 10, SEQ ID NO 12, SEQ ID NO 14, SEQ ID NO 16 or SEQ ID NO 18, b) 10-50 wt % builder selected from citric acid, methyl glycine-N,N-diacetic acid (MGDA) and/or glutamic-N,N-diacetic acid (GLDA) and a second builder selected from carbonates, silicates and zeolites, and c) at least one bleach component.

The bleach component is preferably selected from percarbonates, persulphates and peracids.

One embodiment concerns a dish wash composition comprising:

a) at least 0.01 mg of active protease per gram of composition wherein the protease is selected from a polypeptide comprising SEQ ID NO 2, SEQ ID NO 4, SEQ ID NO 6, SEQ ID NO 8, SEQ ID NO 10, SEQ ID NO 12, SEQ ID NO 14, SEQ ID NO 16 or SEQ ID NO 18, b) 10-50 wt % builder selected from citric acid, methyl glycine-N,N-diacetic acid (MGDA) and/or glutamic-N,N- diacetic acid (GLDA) and a second builder selected from carbonates, silicates and zeolites, and c) at least one bleach component, selected from percarbonates, persulphates and peracids.

The detergent may contain 0-30% by weight, such as about 1% to about 20%, of a bleaching system. Any bleaching system comprising components known in the art for use in cleaning detergents may be utilized. Suitable bleaching system components include sources of hydrogen peroxide; sources of peracids; and bleach catalysts or boosters.

Sources of Hydrogen Peroxide

Suitable sources of hydrogen peroxide are inorganic persalts, including alkali metal salts such as sodium percarbonate and sodium perborates (usually mono- or tetrahydrate), and hydrogen peroxide-urea (1/1).

Sources of Peracids

Peracids may be (a) incorporated directly as preformed peracids or (b) formed in situ in the wash liquor from hydrogen peroxide and a bleach activator (perhydrolysis) or (c) formed in situ in the wash liquor from hydrogen peroxide and a perhydrolase and a suitable substrate for the latter, e.g., an ester.

a) Suitable preformed peracids include, but are not limited to, peroxycarboxylic acids such as peroxybenzoic acid and its ring-substituted derivatives, peroxy-α-naphthoic acid, peroxyphthalic acid, peroxylauric acid, peroxystearic acid, ε-phthalimidoperoxycaproic acid [phthalimidoperoxyhexanoic acid (PAP)], and o-carboxybenzamidoperoxycaproic acid; aliphatic and aromatic diperoxydicarboxylic acids such as diperoxydodecanedioic acid, diperoxyazelaic acid, diperoxysebacic acid, diperoxybrassylic acid, 2-decyldiperoxybutanedioic acid, and diperoxyphthalic, -isophthalic and -terephthalic acids; perimidic acids; peroxymonosulfuric acid; peroxydisulfuric acid; peroxyphosphoric acid; peroxysilicic acid; and mixtures of said compounds. It is understood that the peracids mentioned may in some cases be best added as suitable salts, such as alkali metal salts (e.g., Oxone®) or alkaline earth-metal salts.

b) Suitable bleach activators include those belonging to the class of esters, amides, imides, nitriles or anhydrides and, where applicable, salts thereof. Suitable examples are tetraacetylethylenediamine (TAED), sodium 4-[(3,5,5-trimethylhexanoyl)oxy]benzene-1-sulfonate (ISONOBS), sodium 4-(dodecanoyloxy)benzene-1-sulfonate (LOBS), sodium 4-(decanoyloxy)benzene-1-sulfonate, 4-(decanoyloxy)benzoic acid (DOBA), sodium 4-(nonanoyloxy)benzene-1-sulfonate (NOBS), and/or those disclosed in WO98/17767. A particular family of bleach activators of interest was disclosed in EP624154 and particularly preferred in that family is acetyl triethyl citrate (ATC). ATC or a short chain triglyceride like triacetin has the advantage that they are environmentally friendly. Furthermore acetyl triethyl citrate and triacetin have good hydrolytical stability in the product upon storage and are efficient bleach activators. Finally ATC is multifunctional, as the citrate released in the perhydrolysis reaction may function as a builder.

Bleach Catalysts and Boosters

The bleaching system may also include a bleach catalyst or booster.

Some non-limiting examples of bleach catalysts that may be used in the compositions of the present invention include manganese oxalate, manganese acetate, manganese-collagen, cobalt-amine catalysts and manganese triazacyclononane (MnTACN) catalysts; particularly preferred are complexes of manganese with 1,4,7-trimethyl-1,4,7-triazacyclononane (Me3-TACN) or 1,2,4,7-tetramethyl-1,4,7-triazacyclononane (Me4-TACN), in particular Me3-TACN, such as the dinuclear manganese complex [(Me3-TACN)Mn(O)3Mn(Me3-TACN)](PF6)2, and [2,2',2"-nitrilotris(ethane-1,2-diylazanylylidene-κN-methanylylidene)triphenolato-κ3O]manganese(III). The bleach catalysts may also be other metal compounds, such as iron or cobalt complexes.

In some embodiments, where a source of a peracid is included, an organic bleach catalyst or bleach booster may be used having one of the following formulae:

(i)

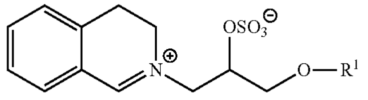

(ii)

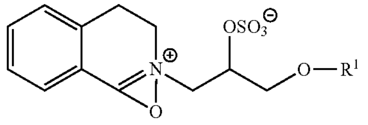

(iii) and mixtures thereof; wherein each R1 is independently a branched alkyl group containing from 9 to 24 carbons or linear alkyl group containing from 11 to 24 carbons, preferably each R1 is independently a branched alkyl group containing from 9 to 18 carbons or linear alkyl group containing from 11 to 18 carbons, more preferably each R1 is independently selected from the group consisting of 2-propylheptyl, 2-butyloctyl, 2-pentylnonyl, 2-hexyldecyl, dodecyl, tetradecyl, hexadecyl, octadecyl, isononyl, isodecyl, isotridecyl and isopentadecyl.

Other exemplary bleaching systems are described, e.g. in WO2007/087258, WO2007/087244, WO2007/087259, EP1867708 (Vitamin K) and WO2007/087242. Suitable photobleaches may for example be sulfonated zinc or aluminium phthalocyanines.

According to one embodiment, the dish wash composition is an automatic dish wash composition (ADW) comprising:

a) at least 0.01 mg of active protease per gram of composition wherein the protease is selected from a polypeptide comprising SEQ ID NO 2, SEQ ID NO 4, SEQ ID NO 6, SEQ ID NO 8, SEQ ID NO 10, SEQ ID NO 12, SEQ ID NO 14, SEQ ID NO 16 or SEQ ID NO 18, and b) 10-50 wt % builder and c) at least one bleach component, wherein the bleach is a peroxide and the bleach catalyst is a manganese compound.

The oxygen bleach is preferably percarbonate and the manganese catalyst preferably 1,4,7-trimethyl-1,4,7-triazacyclononane or manganese (III) acetate tetrahydrate According to one embodiment, the dish wash composition is an automatic dish wash composition (ADW) comprising:

a) at least 0.01 mg of active protease per gram of composition wherein the protease is selected from a polypeptide comprising SEQ ID NO 2, SEQ ID NO 4, SEQ ID NO 6, SEQ ID NO 8, SEQ ID NO 10, SEQ ID NO 12, SEQ ID NO 14, SEQ ID NO 16 or SEQ ID NO 18, and b) 10-50 wt % builder selected from citric acid, methyl glycine-N,N-diacetic acid (MGDA) and/or glutamic-N,N-diacetic acid (GLDA) and mixtures thereof.

c) at least one bleach component, wherein the bleach is an oxygen bleach and the bleach catalyst is a manganese compound.

The oxygen bleach is preferably percarbonate and the manganese catalyst preferably 1,4,7-trimethyl-1,4,7-triazacyclo-nonane or manganese (II) acetate tetrahydrate According to one embodiment, the dish wash composition is an automatic dish wash composition (ADW) comprising:

a) at least 0.01 mg of active protease per gram of composition wherein the protease is selected from a polypeptide comprising SEQ ID NO 2, SEQ ID NO 4, SEQ ID NO 6, SEQ ID NO 8, SEQ ID NO 10, SEQ ID NO 12, SEQ ID NO 14, SEQ ID NO 16 or SEQ ID NO 18, b) 10-50 wt % builder selected from citric acid, methyl glycine-N,N-diacetic acid (MGDA) and/or glutamic-N,N-diacetic acid (GLDA) and mixtures thereof, and c) 0.1-40 wt %, preferably from 0.5-30 wt %, of bleaching components, wherein the bleach components are a peroxide, preferably percabonate and a metal-containing bleach catalyst preferably 1,4,7-trimethyl-1,4,7-triazacyclononane or manganese (II) acetate tetrahydrate (MnTACN).

The dish wash composition may also contain at least one surfactant, preferably anionic or nonionic surfactants but also amphoteric surfactants may be used. In general, bleach-stable surfactants are preferred. Preferred anionic surfactants are sulphate surfactants and in particular alkyl ether sulphates, especially C-9-15 alcohol ethersulfates, C12-15 primary alcohol ethoxylate, C8-C16 ester sulphates and C10-C14 ester sulphates, such as mono dodecyl ester sulphates Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.

The anionic surfactants are preferably added to the detergent in the form of salts. Suitable cations in these salts are alkali metal ions, such as sodium, potassium and lithium and ammonium salts, for example (2-hydroxyethyl) ammonium, bis(2-hydroxyethyl)ammonium and tris(2-hydroxyethyl) ammonium salts.

Non-limiting examples of nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), as well as products available under the trade names SPAN and TWEEN, and combinations thereof.

Commercially available nonionic surfactants includes Plurafac™, Lutensol™ and Pluronic™ range from BASF, Dehypon™ series from Cognis and Genapol™ series from Clariant.

The surfactants useful in the present invention are desirably included in the present detergent compositions at levels of from about 0.1% to about 15%, such as about 2 to about 8% of the composition. The total amount of surfactants typically included in the detergent compositions is typically at least 10% by weight, preferably of from 0.5% to 10% by weight and most preferably from 1% to 5% by weight.

The detergent composition may also be formulated into a granular detergent for laundry.

One embodiment of the invention concerns a granular detergent composition comprising a) at least 0.01 mg of active protease per gram of composition wherein the protease is selected from a polypeptide comprising SEQ ID NO 2, SEQ ID NO 4, SEQ ID NO 6, SEQ ID NO 8, SEQ ID NO 10, SEQ ID NO 12, SEQ ID NO 14, SEQ ID NO 16 or SEQ ID NO 18, b) 5 wt % to 50 wt % anionic surfactant c) 1 wt % to 8 wt % nonionic surfactant d) 5 wt % to 40 wt % builder such as carbonates, zeolites, phosphate builder, calcium sequestering builders or complexing agents The surfactant may be selected among nonionic, anionic and/or amphoteric surfactants as described above, preferably anionic or nonionic surfactants but also amphoteric surfactants may be used. In general, bleach-stable surfactants are preferred. Preferred anionic surfactants are sulphate surfactants and in particular alkyl ether sulphates, especially C-9-15 alcohol ethersulfates, C12-15 primary alcohol ethoxylate, C8-C16 ester sulphates and C10-C14 ester sulphates, such as mono dodecyl ester sulphates Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.

The anionic surfactants are preferably added to the detergent in the form of salts. Suitable cations in these salts are alkali metal ions, such as sodium, potassium and lithium and ammonium salts, for example (2-hydroxyethyl)ammonium, bis(2-hydroxyethyl)ammonium and tris(2-hydroxyethyl) ammonium salts.

Non-limiting examples of nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), as well as products available under the trade names SPAN and TWEEN, and combinations thereof.

Commercially available nonionic surfactants includes Plurafac™, Lutensol™ and Pluronic™ range from BASF, Dehypon™ series from Cognis and Genapol™ series from Clariant. The builder is may be non-phosphate such as citrate preferably as a sodium salt and/or zeolites. Phosphonate builder may be any of those described above The builder is preferably selected among phosphates and sodium citrate builders, sodium carbonate, sodium silicate, sodium aluminosilicate (zeolite) as described above under the dish wash compositions. Suitable builders are described above and include alkali metal or ammonium phosphates, polyphosphates, phosphonates, polyphosphonates, carbonates, bicarbonates, borates, polyhydroxysulfonates, polyacetates, carboxylates, citrates, and polycarboxylates. Citrate builders, e.g., citric acid and soluble salts thereof (particularly sodium salt), are polycarboxylate builders. The builder is preferably added in an amount of about 0-65% by weight, such as about 5% to about 50% by weight, such as 5 to 40% by weight, such as 10 to 40% by weight, such as 10 to 30% by weight, such as 15 to 20% by weight or such as 20 to 40% by weight. The builder may be a phosphonate builder including 1-hydroxyethane-1,1-diphosphonic acid (HEDP), ethylenediaminetetra (methylenephosphonic acid) (EDTMPA), diethylenetriaminepentakis (methylenephosphonic acid) (DTMPA or DTPMPA), diethylenetriamine penta (methylenephosphonic acid) (DTPMP), aminotris(methylenephosphonic acid) (ATMP), 2-phosphonobutane-1,2,4-tricarboxylic acid (PBTC) and hexamethylenediaminetetra (methylenephosphonic acid) (HDTMP).

Preferred phosphonates includes 1-hydroxyethane-1,1-diphosphonic acid (HEDP) and/or diethylenetriaminepentakis (methylenephosphonic acid) (DTMPA or DTPMPA). The phosphonate is preferably added in an amount of about in a level of from about 0.01% to about 10% by weight, preferably from 0.1% to about 5% by weight, more preferably from 0.5% to 3% by weight of the composition.

The laundry composition may also be phosphate free in the instance the preferred builders includes citrate, carbonates and/or sodium aluminosilicate (zeolite).

The proteases of the invention can also be formulated in liquid laundry compositions such as a liquid laundry compositions composition comprising:

a) at least 0.01 mg of active protease per litre detergent wherein the protease is selected from a polypeptide comprising SEQ ID NO 2, SEQ ID NO 4, SEQ ID NO 6, SEQ ID NO 8, SEQ ID NO 10, SEQ ID NO 12, SEQ ID NO 14, SEQ ID NO 16 or SEQ ID NO 18, b) 2 wt % to 60 wt % of at least one surfactant c) 5 wt % to 50 wt % of at least one builder The surfactant may be selected among nonionic, anionic and/or amphoteric surfactants as described above. Preferred surfactants include alkyl ester sulphates, especially C-9-15 alcohol ethersulfates (AES), 012-15 primary alcohol ethoxylate such as alcohol ethoxylates (AE or AEO), sodium toluene sulfonate (STS), sodium dodecyl sulfate (SDS). Commercially available nonionic surfactants includes Plurafac™, Lutensol™ and Pluronic™ range from BASF, Dehypon™ series from Cognis and Genapol™ series from Clariant.

The surfactants useful in the present invention are desirably included in the present detergent compositions at levels of from about 0.1% to about 15%, such as about 2 to about 8% of the composition. The total amount of surfactants typically included in the detergent compositions is typically at least 15% by weight, preferably of from 0.5% to 15% by weight and most preferably from 1% to 10% by weight. The total amount of surfactants typically included in the detergent compositions is typically at least 15% by weight, preferably of from 0.5% to 15% by weight and most preferably from 1% to 10% by weight.

The builder may be selected among nonionic, anionic and/or amphoteric surfactants as described above. One embodiment of the invention concerns a liquid laundry compositions composition comprising:

a) at least 1 mg/L of active protease, wherein the protease is selected from a polypeptide comprising SEQ ID NO 2, SEQ ID NO 4, SEQ ID NO 6, SEQ ID NO 8, SEQ ID NO 10, SEQ ID NO 12, SEQ ID NO 14, SEQ ID NO 16 or SEQ ID NO 18, and b) 1% to 15% by weight of at least one surfactant wherein the surfactant is LAS, AEOS, AEO and/or SLES, and c) at least one builder.

The builder is preferably selected among phosphates and sodium citrate builders, sodium carbonate, sodium silicate, sodium aluminosilicate (zeolite). Suitable builders are described above and include alkali metal or ammonium phosphates, polyphosphates, phosphonates, polyphosphonates, carbonates, bicarbonates, borates, polyhydroxysulfonates, polyacetates, carboxylates, citrates, and polycarboxylates. Citrate builders, e.g., citric acid and soluble salts thereof (particularly sodium salt), are polycarboxylate builders. The builder is preferably added in an amount of about 0-65% by weight, such as about 5% to about 50% by weight. In a dish wash detergent, the level of builder is typically about 40-65% by weight, particularly about 50-65% by weight, particularly from 20% to 50% by weight. The builder may be a phosphonate builder including 1-hydroxyethane-1,1-diphosphonic acid (HEDP), ethylenediaminetetrakis(methylenephosphonic acid) (EDTMPA), diethylenetriaminepentakis(methylenephosphonic acid) (DTMPA or DTPMPA), diethylenetriaminepentakis(methylenephosphonic acid) (DTPMP), aminotris(methylenephosphonic acid) (ATMP), 2-phosphonobutane-1,2,4-tricarboxylic acid (PBTC) and hexamethylenediaminetetrakis(methylenephosphonic acid) (HDTMP).

Preferred phosphonates includes 1-hydroxyethane-1,1-diphosphonic acid (HEDP) and/or diethylenetriaminepentakis (methylenephosphonic acid) (DTMPA or DTPMPA). The phosphonate is preferably added in an amount of about in a level of from about 0.01% to about 10% by weight, preferably from 0.1% to about 5% by weight, more preferably from 0.5% to 3% by weight of the composition. Additional useful builders are described in the dish wash composition section.

The laundry composition may also be phosphate free in the instance the preferred builders includes citrate and/or methylglycine-N,N-diacetic acid (MGDA) and/or glutamic-N,N-diacetic acid (GLDA) and/or salts thereof.

One embodiment of the invention concerns a liquid laundry compositions composition comprising:

a) at least 0.01 mg of active protease per litre of composition wherein the protease is selected from a polypeptide comprising SEQ ID NO 2, SEQ ID NO 4, SEQ ID NO 6, SEQ ID NO 8, SEQ ID NO 10, SEQ ID NO 12, SEQ ID NO 14, SEQ ID NO 16 or SEQ ID NO 18, and b) 1% to 15% by weight of at least one surfactant wherein the surfactant is LAS, AEOS and/or SLES, and c) 5% to 50% by weight of at least one builder selected from HEDP, DTMPA or DTPMPA.

The detergent compositions of the invention may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or anti-foaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly(ethyleneimine), (carboxymethyl) inulin (CMI), and polycarboxylates such as PAA, PAA/PMA, polyaspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly(oxyethene terephthalate) (PET-POET), PVP, poly(vinylimidazole) (PVI), poly(vinylpyridine-N-oxide) (PVPO or PVPNO) and polyvinylpyrrolidone-vinylimidazole (PVPVI). Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated.

The detergent compositions of the present invention may also include fabric hueing agents such as dyes or pigments, which when formulated in detergent compositions can deposit onto a fabric when said fabric is contacted with a wash liquor comprising said detergent compositions and thus altering the tint of said fabric through absorption/reflection of visible light. Fluorescent whitening agents emit at least some visible light if subjected to ultraviolet light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO2005/03274, WO2005/03275, WO2005/03276 and EP1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g. WO 2007/087257 and WO2007/087243.

The detergent may contain 0-10% by weight, for example 0-5% by weight, such as about 0.5 to about 5%, or about 3% to about 5%, of a hydrotrope. Any hydrotrope known in the art for use in detergents may be utilized. Non-limiting examples of hydrotropes include sodium benzenesulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

The detergent compositions of the present invention can also contain dispersants. In particular powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

The detergent compositions of the present invention may also include one or more dye transfer inhibiting agents. Suitable polymeric dye transfer inhibiting agents include, but are not limited to, polyvinylpyrrolidone polymers, polyamine-N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

The detergent compositions of the present invention will preferably also contain additional components that may tint articles being cleaned, such as fluorescent whitening agent or optical brighteners. Where present the brightener is preferably at a level of about 0.01% to about 0.5%. Any fluorescent whitening agent suitable for use in a laundry detergent composition may be used in the laundry composition of the present invention. The most commonly used fluorescent whitening agents are those belonging to the classes of diaminostilbene-sulfonic acid derivatives, diarylpyrazoline derivatives and biphenyl-distyryl derivatives. Examples of the diaminostilbene-sulfonic acid derivative type of fluorescent whitening agents include the sodium salts of: 4,4'-bis[(4-anilino-6-diethanolamino-s-triazin-2-yl) amino]stilbene-2,2'-disulfonate, 4,4'-bis[(4,6-dianilino-s-triazin-2-yl)amino]stilbene-2,2'-disulfonate, 4,4'-bis{4-anilino-6-[methyl(2-hydroxyethyl)amino]-s-triazin-2-ylamino}stilbene-2,2'-disulfonate, 4,4'-bis(4-phenyl-1,2,3-triazol-2-yl)stilbene-2,2'-disulfonate and sodium 5-(2H-naphtho[1,2-d][1,2,3]triazol-2-yl)-2-[(E)-2-phenylvinyl] benzenesulfonate. Preferred fluorescent whitening agents are Tinopal DMS and Tinopal CBS available from BASF. Tinopal DMS is the disodium salt of 4,4'-bis[(4-anilino-6-morpholino-s-triazin-2-yl)amino]stilbene-2,2'-disulfonate. Tinopal CBS is the disodium salt of 2,2'-[biphenyl-4,4'-di(2,1-ethenediyl)]dibenzene-1-sulfonate. Also preferred is the commercially available Parawhite KX, supplied by Paramount Minerals and Chemicals, Mumbai, India. Other fluorescers suitable for use in the invention include the 1-3-diarylpyrazolines and the 7-alkylaminocoumarins.

Suitable fluorescent brightener levels include lower levels of from about 0.01, from 0.05, from about 0.1 or even from about 0.2 wt % to upper levels of 0.5 or even 0.75 wt %.

The detergent compositions of the present invention may also include one or more soil-release polymers which aid the removal of soils from fabrics such as cotton and polyester-based fabrics, in particular the removal of hydrophobic soils from polyester-based fabrics. The soil release polymers may for example be nonionic or anionic terephthalate-based polymers, polyvinylcaprolactam and related copolymers, vinyl graft copolymers or polyester polyamides; see for example Chapter 7 in Powdered Detergents, Surfactant science series volume 71, Marcel Dekker, Inc. Another type of soil release polymers are amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore random graft co-polymers are suitable soil-release polymers. Suitable graft co-polymers are described in more detail in WO 2007/138054, WO 2006/108856 and WO 2006/113314 (hereby incorporated by reference). Other soil-release polymers are substituted polysaccharide structures especially substituted cellulosic structures such as modified cellulose derivatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof.

The detergent compositions of the present invention may also include one or more anti-redeposition agents such as (carboxymethyl) cellulose (CMC), poly(vinyl alcohol) (PVA), homopolymers of acrylic acid, copolymers of acrylic acid and maleic acid, and ethoxylated polyethyleneimines. The cellulose based polymers described under soil-release polymers above may also function as anti-redeposition agents.

The detergent composition of the invention may also contain one are more adjunct material. Suitable adjunct materials include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

In addition to the proteases with the amino acid sequences SEQ ID NO 2, SEQ ID NO 4, SEQ ID NO 6, SEQ ID NO 8, SEQ ID NO 10, SEQ ID NO 12, SEQ ID NO 14, SEQ ID NO 16 or SEQ ID NO 18 the detergents of the invention may further comprise cellulases. Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having color care benefits. Examples of such cellulases are cellulases described in EP 0 495 257, EP 0 531 372, WO 96/11262, WO 96/29397, WO 98/08940. Other examples are cellulase polypeptides such as those described in WO 94/07998, EP 0 531 315, U.S. Pat. No. 5,457,046, 5,686,593, 5,763,254, WO 95/24471, WO 98/12307 and PCT/DK98/00299.

Example of cellulases exhibiting endo-beta-1,4-glucanase activity (EC 3.2.1.4) are those having described in WO02/099091.

Other examples of cellulases include the family 45 cellulases described in WO96/29397, and especially polypeptides thereof having substitution, insertion and/or deletion at one or more of the positions corresponding to the following positions in SEQ ID NO: 8 of WO 02/099091:2, 4, 7, 8, 10, 13, 15, 19, 20, 21, 25, 26, 29, 32, 33, 34, 35, 37, 40, 42, 42a, 43, 44, 48, 53, 54, 55, 58, 59, 63, 64, 65, 66, 67, 70, 72, 76, 79, 80, 82, 84, 86, 88, 90, 91, 93, 95, 95d, 95h, 95j, 97, 100, 101, 102, 103, 113, 114, 117, 119, 121, 133, 136, 137, 138, 139, 140a, 141, 143a, 145, 146, 147, 150e, 150j, 151, 152, 153, 154, 155, 156, 157, 158, 159, 160c, 160e, 160k, 161, 162, 164, 165, 168, 170, 171, 172, 173, 175, 176, 178, 181, 183, 184, 185, 186, 188, 191, 192, 195, 196, 200, and/or 20, preferably selected among P19A, G20K, Q44K, N48E, Q119H or Q146R.

Commercially available cellulases include Celluzyme™, Celluclean and Carezyme™ (Novozymes A/S), Clazinase™, and Puradax HA™ (Genencor International Inc.), and KAC-500(B)™ (Kao Corporation).

In addition to the proteases with the amino acid sequences SEQ ID NO 2, SEQ ID NO 4, SEQ ID NO 6, SEQ ID NO 8, SEQ ID NO 10, SEQ ID NO 12, SEQ ID NO 14, SEQ ID NO 16 or SEQ ID NO 18 the detergents of the invention may further comprise additional proteases wherein the proteases include those of bacterial, fungal, plant, viral or animal origin e.g. vegetable or microbial origin. Microbial origin is preferred. Chemically modified or protein engineered mutants are included. It may be an alkaline protease, such as a serine protease or a metalloprotease. A serine protease may for example be of the S1 family, such as trypsin, or the S8 family such as subtilisin. A metalloproteases protease may for example be a thermolysin from e.g. family M4 or other metalloprotease such as those from M5, M7 or M8 families.

Subtilases such as those derived from *Bacillus* such as *Bacillus lentus, B. alkalophilus, B. subtilis, B. amyloliquefaciens, Bacillus pumilus* and *Bacillus gibsonii* described in; U.S. Pat. No. 7,262,042 and WO09/021867, and subtilisin lentus, subtilisin Novo, subtilisin Carlsberg, *Bacillus licheniformis*, subtilisin BPN', subtilisin 309, subtilisin 147 and subtilisin 168 described in WO89/06279 and protease PD138 described in (WO93/18140). Other useful proteases may be those described in WO92/175177, WO01/016285, WO02/026024 and WO02/016547. Examples of trypsin-like proteases are trypsin (e.g. of porcine or bovine origin) and the *Fusarium* protease described in WO89/06270, WO94/25583 and WO05/040372, and the chymotrypsin proteases derived from *Cellumonas* described in WO05/052161 and WO05/052146.

A further preferred protease is the alkaline protease from *Bacillus lentus* DSM 5483, as described for example in WO95/23221, and polypeptides thereof which are described in WO92/21760, WO95/23221, EP1921147 and EP1921148.

Examples of metalloproteases are the neutral metalloprotease as described in WO07/044993 (Genencor Int.) such as those derived from *Bacillus amyloliquefaciens*. Examples of useful proteases are the polypeptides described in: WO92/19729, WO96/034946, WO98/20115, WO98/20116, WO99/011768, WO01/44452, WO03/006602, WO04/03186, WO04/041979, WO07/006305, WO11/036263, WO11/036264.

Suitable commercially available protease enzymes include those sold under the trade names Alcalase®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Neutrase®, Everlase® and Esperase® (Novozymes A/S), those sold under the tradename Maxatase®, Maxacal®, Maxapem®, Purafect®, Purafect Prime®, Purafect MA®, Purafect Ox®, Purafect OxP®, Puramax®, Properase®, FN2®, FN3®, FN4®, Excellase®, Opticlean® and Optimase® (Danisco/DuPont), Axapem™ (Gist-Brocases N.V.), BLAP (sequence shown in FIG. 29 of U.S. Pat. No. 5,352,604) and polypeptides hereof (Henkel AG) and KAP (*Bacillus alkalophilus* subtilisin) from Kao.

In addition to the proteases with the amino acid sequences SEQ ID NO 2, SEQ ID NO 4, SEQ ID NO 6, SEQ ID NO 8, SEQ ID NO 10, SEQ ID NO 12, SEQ ID NO 14, SEQ ID NO 16 or SEQ ID NO 18 the detergents of the invention may further comprise lipases and cutinases which include those of bacterial or fungal origin. Chemically modified or protein engineered mutant enzymes are included. Examples include lipase from *Thermomyces*, e.g. from *T. lanuginosus* (previously named *Humicola lanuginosa*) as described in EP258068 and EP305216, cutinase from *Humicola*, e.g. *H. insolens* (WO96/13580), lipase from strains of *Pseudomonas* (some of these now renamed to *Burkholderia*), e.g. *P. alcaligenes* or *P. pseudoalcaligenes* (EP218272), *P. cepacia* (EP331376), *P.* sp. strain SD705 (WO95/06720 & WO96/27002), *P. wisconsinensis* (WO96/12012), GDSL-type *Streptomyces* lipases (WO10/065455), cutinase from *Magnaporthe grisea* (WO10/107560), cutinase from *Pseudomonas mendocina* (U.S. Pat. No. 5,389,536), lipase from *Thermobifida fusca* (WO11/084412), *Geobacillus stearothermophilus* lipase (WO11/084417), lipase from *Bacillus subtilis* (WO11/084599), and lipase from *Streptomyces griseus* (WO11/150157) and *S. pristinaespiralis* (WO12/137147).

Other examples are lipase polypeptides such as those described in EP407225, WO92/05249, WO94/01541, WO94/25578, WO95/14783, WO95/30744, WO95/35381, WO95/22615, WO96/00292, WO97/04079, WO97/07202, WO00/34450, WO00/60063, WO01/92502, WO07/87508 and WO09/109500.

Preferred commercial lipase products include include Lipolase™, Lipex™; Lipolex™ and Lipoclean™ (Novozymes A/S), Lumafast (originally from Genencor) and Lipomax (originally from Gist-Brocades).

Still other examples are lipases sometimes referred to as acyltransferases or perhydrolases, e.g. acyltransferases with homology to *Candida antarctica* lipase A (WO10/111143), acyltransferase from *Mycobacterium smegmatis* (WO05/56782), perhydrolases from the CE 7 family (WO09/67279), and polypeptides of the *M. smegmatis* perhydrolase in particular the S54V variant used in the commercial product Gentle Power Bleach from Huntsman Textile Effects Pte Ltd (WO10/100028).

In addition to the proteases with the amino acid sequences SEQ ID NO 2, SEQ ID NO 4, SEQ ID NO 6, SEQ ID NO 8, SEQ ID NO 10, SEQ ID NO 12, SEQ ID NO 14, SEQ ID NO 16 or SEQ ID NO 18 the detergents of the invention may further comprise amylases which can be used together with a proteases of the invention. The amylase may be an alpha-amylase or a glucoamylase and may be of bacterial or fungal origin. Chemically modified or protein engineered mutants are included. Amylases include, for example, alpha-amylases obtained from *Bacillus*, e.g., a special strain of *Bacillus licheniformis*, described in more detail in GB 1,296,839.

Suitable amylases include amylases having SEQ ID NO: 3 in WO 95/10603 or polypeptides having 90% sequence identity to SEQ ID NO: 3 thereof. Preferred polypeptides are described in WO 94/02597, WO 94/18314, WO 97/43424 and SEQ ID NO: 4 of WO 99/019467, such as polypeptides with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444.

Different suitable amylases include amylases having SEQ ID NO: 6 in WO 02/010355 or polypeptides thereof having 90% sequence identity to SEQ ID NO: 6. Preferred polypeptides of SEQ ID NO: 6 are those having a deletion in positions 181 and 182 and a substitution in position 193.

Other amylases which are suitable are hybrid alpha-amylase comprising residues 1-33 of the alpha-amylase derived from *B. amyloliquefaciens* shown in SEQ ID NO: 6 of WO 2006/066594 and residues 36-483 of the *B. licheniformis* alpha-amylase shown in SEQ ID NO: 4 of WO 2006/066594 or polypeptides having 90% sequence identity thereof. Preferred polypeptides of this hybrid alpha-amylase are those having a substitution, a deletion or an insertion in one of more of the following positions: G48, T49, G107, H156, A181, N190, M197, I201, A209 and Q264. Most preferred polypeptides of the hybrid alpha-amylase comprising residues 1-33 of the alpha-amylase derived from *B. amyloliquefaciens* shown in SEQ ID NO: 6 of WO 2006/066594 and residues 36-483 of SEQ ID NO: 4 are those having the substitutions:

M197T;

H156Y+A181T+N190F+A209V+Q264S; or

G48A+T49I+G107A+H156Y+A181T+N190F+I201F+A209V+Q264S.

Further amylases which are suitable are amylases having SEQ ID NO: 6 in WO 99/019467 or polypeptides thereof having 90% sequence identity to SEQ ID NO: 6. Preferred polypeptides of SEQ ID NO: 6 are those having a substitution, a deletion or an insertion in one or more of the following positions: R181, G182, H183, G184, N195, I206, E212, E216 and K269. Particularly preferred amylases are those having deletion in positions R181 and G182, or positions H183 and G184.

Additional amylases which can be used are those having SEQ ID NO: 1, SEQ ID NO: 3, SEQ ID NO: 2 or SEQ ID NO: 7 of WO 96/023873 or polypeptides thereof having 90% sequence identity to SEQ ID NO: 1, SEQ ID NO: 2, SEQ ID NO: 3 or SEQ ID NO: 7. Preferred polypeptides of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476. More preferred polypeptides are those having a deletion in positions 181 and 182 or positions 183 and 184. Most preferred amylase polypeptides of SEQ ID NO: 1, SEQ ID NO: 2 or SEQ ID NO: 7 are those having a deletion in positions 183 and 184 and a substitution in one or more of positions 140, 195, 206, 243, 260, 304 and 476.

Other amylases which can be used are amylases having SEQ ID NO: 2 of WO 08/153815, SEQ ID NO: 10 in WO 01/66712 or polypeptides thereof having 90% sequence identity to SEQ ID NO: 2 of WO 08/153815 or 90% sequence identity to SEQ ID NO: 10 in WO 01/66712. Preferred polypeptides of SEQ ID NO: 10 in WO 01/66712 are those having a substitution, a deletion or an insertion in one of more of the following positions: 176, 177, 178, 179, 190, 201, 207, 211 and 264.

Further suitable amylases are amylases having SEQ ID NO: 2 of WO 09/061380 or polypeptides having 90% sequence identity to SEQ ID NO: 2 thereof. Preferred polypeptides of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred polypeptides of SEQ ID NO: 2 are those having the substitution in one of more of the following positions: Q87E,R, Q98R, S125A, N128C, T131I, T165I, K178L, T182G, M201L, F202Y, N225E,R, N272E,R, S243Q,A,E,D, Y305R, R309A, Q320R, Q359E, K444E and G475K and/or deletion in position R180 and/or S181 or of T182 and/or G183. Most preferred amylase polypeptides of SEQ ID NO: 2 are those having the substitutions:

N128C+K178L+T182G+Y305R+G475K;

N128C+K178L+T182G+F202Y+Y305R+D319T+G475K;

S125A+N128C+K178L+T182G+Y305R+G475K; or

S125A+N128C+T131I+T165I+K178L+T182G+Y305R+G475K wherein the polypeptides are C-terminally truncated and optionally further comprises a substitution at position 243 and/or a deletion at position 180 and/or position 181.

Other suitable amylases are the alpha-amylase having SEQ ID NO: 12 in WO01/66712 or a variant having at least 90% sequence identity to SEQ ID NO: 12. Preferred amylase polypeptides are those having a substitution, a deletion or an insertion in one of more of the following positions of SEQ ID NO: 12 in WO01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include polypeptides having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions.

Other examples are amylase polypeptides such as those described in WO2011/098531, WO2013/001078 and WO2013/001087.

Commercially available amylases are Duramyl™, Termamyl™, Fungamyl™, Stainzyme™, Stainzyme Plus™, Natalase™, Liquozyme X and BAN™ (from Novozymes A/S), and Rapidase™, Purastar™/Effectenz™, Powerase and Preferenz S100 (from Genencor International Inc./DuPont).

In addition to the proteases with the amino acid sequences SEQ ID NO 2, SEQ ID NO 4, SEQ ID NO 6, SEQ ID NO 8, SEQ ID NO 10, SEQ ID NO 12, SEQ ID NO 14, SEQ ID NO 16 or SEQ ID NO 18 the detergents of the invention may further comprise peroxidases/oxidases including those of plant, bacterial or fungal origin. Chemically modified or protein engineered mutants are included. Examples of useful peroxidases include peroxidases from *Coprinus*, e.g., from *C. cinereus*, and polypeptides thereof as those described in WO 93/24618, WO 95/10602, and WO 98/15257.

Commercially available peroxidases include Guardzyme™ (Novozymes A/S).

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a homogenous tablet, a tablet having two or more layers, a pouch having one or more compartments, a regular or compact powder, a granule, a paste, a gel, or a regular, compact or concentrated liquid.

Pouches can be configured as single or multicompartments. It can be of any form, shape and material which is suitable for hold the composition, e.g. without allowing the release of the composition to release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxypropyl methyl cellulose (HPMC). Preferably the level of polymer in the film for example PVA is at least about 60%. Preferred average molecular weight will typically be about 20,000 to about 150,000. Films can also be of blended compositions comprising hydrolytically degradable and water soluble polymer blends such as polylactide and polyvinyl alcohol (known under the Trade reference M8630 as sold by MonoSol LLC, Indiana, USA) plus plasticisers like glycerol, ethylene glycerol, propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids: US2009/0011970 A1.

Detergent ingredients can be separated physically from each other by compartments in water dissolvable pouches or in different layers of tablets. Thereby negative storage interaction between components can be avoided. Different dissolution profiles of each of the compartments can also give rise to delayed dissolution of selected components in the wash solution.

A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent.

The present invention is also directed to methods for using the polypeptides according to the invention or compositions thereof in laundering of textile and fabrics, such as house hold laundry washing and industrial laundry washing.

The invention is also directed to methods for using the polypeptides according to the invention or compositions thereof in cleaning hard surfaces such as floors, tables, walls, roofs etc. as well as surfaces of hard objects such as cars (car wash) and dishes (dish wash).

The polypeptides of the present invention may be added to and thus become a component of a detergent composition. Thus one aspect of the invention relates to the use of a polypeptide comprising the SEQ ID NO 2, SEQ ID NO 4, SEQ ID NO 6, SEQ ID NO 8, SEQ ID NO 10, SEQ ID NO 12, SEQ ID NO 14, SEQ ID NO 16 and SEQ ID NO 18 in a cleaning process such as laundering and/or hard surface cleaning.

Thus one aspect of the invention relates to the use of the use of a polypeptide comprising the SEQ ID NO 2, SEQ ID NO 4, SEQ ID NO 6, SEQ ID NO 8, SEQ ID NO 10, SEQ ID NO 12, SEQ ID NO 14, SEQ ID NO 16 and SEQ ID NO 18 in a cleaning process such as laundering and/or hard surface cleaning and wherein the polypeptide has improved wash performance, relative to a reference enzyme such as a protease with SEQ ID NO 19.

The cleaning process or the textile care process may for example be a laundry process, a dishwashing process or cleaning of hard surfaces such as bathroom tiles, floors, table tops, drains, sinks and washbasins. Laundry processes can for example be household laundering, but it may also be industrial laundering. Furthermore, the invention relates to a process for laundering of fabrics and/or garments where the process comprises treating fabrics with a washing solution containing a detergent composition, and at least one protease variant of the invention. The cleaning process or a textile care process can for example be carried out in a machine washing process or in a manual washing process. The washing solution can for example be an aqueous washing solution containing a detergent composition.

The last few years there has been an increasing interest in replacing components in detergents, which is derived from petrochemicals with renewable biological components such as enzymes and polypeptides without compromising the wash performance. When the components of detergent compositions change new enzyme activities or new enzymes having alternative and/or improved properties compared to the common used detergent enzymes such as proteases, lipases and amylases are needed to achieve a similar or improved wash performance when compared to the traditional detergent compositions.

The invention further concerns the use of polypeptides of the invention in a proteinaceous stain removing processes. The proteinaceous stains may be stains such as food stains, e.g., baby food, sebum, cocoa, egg, blood, milk, ink, grass or a combination hereof, and more specific such as egg yolk, minced meat, Crème Brûlée, pasta, burnt-in milk. The protease comprising the amino acid sequences SEQ ID NO 2, SEQ ID NO 4, SEQ ID NO 6, SEQ ID NO 8, SEQ ID NO 10, SEQ ID NO 12, SEQ ID NO 14, SEQ ID NO 16 or SEQ ID NO 18 and in particular the proteases comprising SEQ ID NO 2 and SEQ ID NO 4 are active on blood stains in particular aged blood and heat treated blood stains such as blood/milk/ink. Blood stains are particular resistant stain to remove and on the same time commercially very relevant e.g. in industrial cleaning. Often blood soiled textiles are not immediately washed and being exposed to elevated temperatures thus wash performance or stain removal properties on such stains are advantageous in particular in textile cleaning. One aspect of the invention relates to a protease comprising the amino acid sequences SEQ ID NO 2, SEQ ID NO 4, SEQ ID NO 6, SEQ ID NO 8, SEQ ID NO 10, SEQ ID NO 12, SEQ ID NO 14, SEQ ID NO 16 or SEQ ID NO 18 wherein the protease have improved wash performance on blood stains compared to the protease with SEQ ID NO 19. A particular aspect of the invention relates to the use of a protease comprising or consisting of the amino acid sequences SEQ ID NO 2, SEQ ID NO 4, SEQ ID NO 6, SEQ ID NO 8, SEQ ID NO 10, SEQ ID NO 12, SEQ ID NO 14, SEQ ID NO 16 or SEQ ID NO 18 for removal of blood stains from textiles.

In a particular embodiment, the invention concerns the use of a composition comprising the polypeptides of the invention and one or more detergent components, such as surfactants, hydrotropes, builders, co-builders, chelators or chelating agents, bleaching system or bleach components, polymers, fabric hueing agents, fabric conditioners, foam boosters, suds suppressors, dispersants, dye transfer inhibitors, fluorescent whitening agents, perfume, optical brighteners, bactericides, fungicides, soil suspending agents, soil release polymers, anti-redeposition agents, enzyme inhibitors or stabilizers, enzyme activators, antioxidants, and solubilizers.

In a particular embodiment, the invention concerns the use of a composition comprising a subtilase variant of the invention and one or more additional enzymes selected from the group consisting of proteases, amylases, lipases, cutinases, cellulases, endoglucanases, xyloglucanases, pectinases, pectin lyases, xanthanases, peroxidaes, haloperoxygenases, catalases and mannanases, or any mixture thereof.

In a particular embodiment, the invention concerns the use of a composition comprising a subtilase variant of the invention, one or more additional enzymes selected from the group consisting of proteases, amylases, lipases, cutinases, cellulases, endoglucanases, xyloglucanases, pectinases, pectin lyases, xanthanases, peroxidaes, haloperoxygenases, catalases and mannanases, or any mixture thereof and one or more detergent components, such as surfactants, hydrotropes, builders, co-builders, chelators or chelating agents, bleaching system or bleach components, polymers, fabric hueing agents, fabric conditioners, foam boosters, suds suppressors, dispersants, dye transfer inhibitors, fluorescent whitening agents, perfume, optical brighteners, bactericides, fungicides, soil suspending agents, soil release polymers, anti-redeposition agents, enzyme inhibitors or stabilizers, enzyme activators, antioxidants, and solubilizers.

Washing Method

The present invention also relates to a method of cleaning a fabric, a dishware or hard surface with a detergent composition comprising a polypeptide of the invention.

A preferred embodiment concerns a method of cleaning, said method comprising the steps of: contacting an object with a detergent composition comprising a polypeptide of the invention under conditions suitable for cleaning said object. In a preferred embodiment the detergent composition is used in a laundry or a dish wash process.

Still another embodiment relates to a method for removing stains from fabric or dishware which comprises contacting said fabric or dishware with a composition comprising a polypeptide of the invention under conditions suitable for cleaning said object.

Also contemplated are compositions and methods of treating fabrics (e.g., to desize a textile) using one or more of the protease of the invention. The protease can be used in any fabric-treating method which is well known in the art (see, e.g., U.S. Pat. No. 6,077,316). For example, in one aspect, the feel and appearance of a fabric is improved by a method comprising contacting the fabric with a protease in a solution. In one aspect, the fabric is treated with the solution under pressure.

The detergent compositions of the present invention are suited for use in laundry and hard surface applications, including dish wash. Accordingly, the present invention includes a method for laundering a fabric or washing dishware. The method comprises the steps of contacting the fabric/dishware to be cleaned with a solution comprising the detergent composition according to the invention. The fabric may comprise any fabric capable of being laundered in normal consumer use conditions. The dishware may comprise any dishware such as crockery, cutlery, ceramics, plastics such as melamine, metals, china, glass and acrylics. The solution preferably has a pH from about 5.5 to about 11.5. The compositions may be employed at concentrations from about 100 ppm, preferably 500 ppm to about 15,000 ppm in solution. The water temperatures typically range from about 5° C. to about 95° C., including about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C. and about 90° C.

Variations in local and regional conditions, such as water hardness and wash temperature call for regional detergent compositions. Table 1 provide ranges for the composition of a typical European automatic dish wash (ADW) detergent.

TABLE 1

| Typical European ADW detergent composition | |
|---|---|
| P-Containing formulation | P-Free formulations |
| 20-50% STPP | 10-20% Na Citrate (or Chelating agent) |
| 15-45% Soda (sodium carbonate) | 25% Soda (sodium carbonate) |
| 5-15% Sodium percabonate | 5-10% Sodium percabonate |
| 0-20% Sodium disilicate | 5-25% Sodium disilicate |
| 2-3% TAED | 0-3% TAED |
| 2-6% Polymers | 2-6% Polymers |
| 1-2% Phosphonate | 1-20% Sodium sulfate |
| 3-5% Surfactants | <5% Surfactants |
| <5% Enzymes | <5% Enzymes |
| To 100% Rest (perfume, dye, corrosion inhibitor. etc.) pH 9-11 | To 100% Rest (perfume, dye, corrosion inhibitor. etc.) pH 9-11 |

The polypeptides of the detergent composition of the invention may be stabilized using conventional stabilizing agents and protease inhibitors, e.g. a polyol such as propylene glycol or glycerol, a sugar or sugar alcohol, different salts such as NaCl; KCl; lactic acid, formic acid, boric acid, or a boric acid derivative, e.g., an aromatic borate ester, or a phenyl boronic acid derivative such as 4-formylphenyl boronic acid, or a peptide aldehyde such as di-, tri- or tetrapeptide aldehydes or aldehyde analogues (either of the form B1-B0-R wherein, R is H, CH3, CX3, CHX2, or CH2X (X=halogen), B0 is a single amino acid residue (preferably with an optionally substituted aliphatic or aromatic side chain); and B1 consists of one or more amino acid residues (preferably one, two or three), optionally comprising an N-terminal protection group, or as described in WO09118375, WO98/13459) or a protease inhibitor of the protein type such as RASI, BASI, WASI (bifunctional alpha-amylase/subtilisin inhibitors of rice, barley and wheat) or CI2 or SSI. The composition may be formulated as described in e.g. WO 92/19709, WO 92/19708 and U.S. Pat. No. 6,472,364. In some embodiments, the enzymes employed herein are stabilized by the presence of water-soluble sources of zinc (II), calcium (II) and/or magnesium (II) ions in the finished compositions that provide such ions to the enzymes, as well as other metal ions (e.g., barium (II), scandium (II), iron (II), manganese (II), aluminum (III), Tin (II), cobalt (II), copper (II), Nickel (II), and oxovanadium (IV)).

In one embodiment, the polypeptides are stabilized using peptide aldehydes or ketones Suitable peptide aldehydes are described in WO94/04651, WO95/25791, WO98/13458, WO98/13459, WO98/13460, WO98/13461, WO98/13462, WO07/141736, WO07/145963, WO09/118375, WO10/055052 and WO11/036153. A polypeptide of the present invention may also be incorporated in the detergent formulations disclosed in WO 97/07202, which is hereby incorporated by reference.

In another embodiment, the polypeptides are stabilized using a phenyl boronic acid derivative is 4-formylphenylboronic acid (4-FPBA) with the following formula:

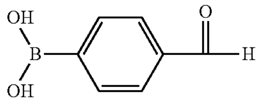 [SMILES: O=Cc1ccc(B(O)O)cc1]

The detergent compositions may comprise two or more stabilizing agents e.g. such as those selected from the group consisting of propylene glycol, glycerol, 4-formylphenyl boronic acid and borate.

The stabilizing agent(s) is preferably present in the detergent composition in a quantity of from 0.001 to about 5.0 wt %, from 0.01 to about 2.0 wt %, from 0.1 to about 3 wt % or from 0.5% to about 1.5 wt %.

In some preferred embodiments, the detergent compositions provided herein are typically formulated such that, during use in aqueous cleaning operations, the wash water has a pH of from about 5.0 to about 11.5, or in alternative embodiments, even from about 6.0 to about 10.5. In some preferred embodiments, granular or liquid laundry products are formulated to have a pH from about 6 to about 8. Techniques for controlling pH at recommended usage levels include the use of buffers, alkalis, acids, etc., and are well known to those skilled in the art.

The present invention is further described by the following examples that should not be construed as limiting the scope of the invention.

EXAMPLES

Materials and Methods

Protease Assay (Suc-AAPF-pNA assay)

pNA substrate: Suc-AAPF-pNA (Bachem L-1400).

Temperature: Room temperature (25° C.)

Assay buffer: 100 mM succinic acid, 100 mM HEPES, 100 mM CHES, 100 mM CABS, 1 mM $CaCl_2$, 150 mM KCL, 0.01% Triton X-100, pH 9.0.

20 μl protease (diluted in 0.01% Triton X-100) was mixed with 100 μl assay buffer. The assay was started by adding 100 μl pNA substrate (50 mg dissolved in 1.0 ml DMSO and further diluted 45× with 0.01% Triton X-100). The increase in $OD_{405}$ was monitored as a measure of the protease activity.

Example 1: Preparation and Expression of Polypeptides

The following summarizes the mutation and introduction of an expression cassette into *Bacillus subtilis*. All DNA manipulations were done by PCR (e.g. Sambrook et al.; Molecular Cloning; Cold Spring Harbor Laboratory Press) and can be repeated by everybody skilled in the art.

Recombinant *B. subtilis* constructs encoding subtilase polypeptides were used to inoculate shakeflasks containing a rich media (e.g. PS-1: 100 g/L Sucrose (Danisco cat. no. 109-0429), 40 g/L crust soy (soy bean flour), 10 g/L Na2HPO4.12H2O (Merck cat. no. 6579), 0.1 ml/L replace-Dowfax63N10 (Dow). Cultivation typically takes 4 days at 30° C. shaking with 220 rpm.

Example 2: Fermentation of Polypeptides

Fermentation may be performed by methods well known in the art or as follows. A *B. subtilis* strain harboring the relevant expression plasmid was streaked on a LB agar plate, and grown overnight at 37° C. The colonies were transferred to 100 ml PS-1 media in a 500 ml shaking flask. Cells and other undissolved material were removed from the fermentation broth by centrifugation at 4500 rpm for 20-25 minutes. Afterwards the supernatant was filtered to obtain a clear solution.

Example 3: Purification of Polypeptides

The culture broth was centrifuged (26000×g, 20 min) and the supernatant was carefully decanted from the precipitate. The supernatant was filtered through a Nalgene 0.2 μm filtration unit in order to remove the rest of the *Bacillus* host cells. pH in the 0.2 μm filtrate was adjusted to pH 8 with 3M Tris base and the pH adjusted filtrate was applied to a MEP Hypercel column (from Pall corporation) equilibrated in 20 mM Tris/HCl, 1 mM $CaCl_2$, pH 8.0. After washing the column with the equilibration buffer, the column was step-eluted with 20 mM $CH_3COOH$/NaOH, 1 mM $CaCl_2$, pH 4.5. Fractions from the column were analysed for protease activity (using the Suc-AAPF-pNA assay at pH 9) and peak-fractions were pooled. The pH of the pool from the MEP Hypercel column was adjusted to pH 6 with 20% (v/v) $CH_3COOH$ or 3M Tris base and the pH adjusted pool was diluted with deionized water to the same conductivity as 20 mM MES/NaOH, 2 mM $CaCl_2$, pH 6.0. The diluted pool was applied to a SP-sepharose FF column (from GE Healthcare) equilibrated in 20 mM MES/NaOH, 2 mM $CaCl_2$, pH 6.0. After washing the column with the equilibration buffer, the protease was eluted with a linear NaCl gradient (0→0.5M) in the same buffer over five column volumes. Fractions from the column were analysed for protease activity (using the Suc-AAPF-pNA assay at pH 9) and active fractions were analysed by SDS-PAGE. The fractions, where only one band was seen on the coomassie stained SDS-PAGE gel, were pooled as the purified preparation and was used for further experiments.

Example 4: In Wash Stability

In Wash Stability Assay

In wash stability was measured according to the 'In wash stability assay' as described below using the MGDA and STPP model detergents as defined in table 2. The results are Presented in table 2.

TABLE 2

Composition of the MGDA and STPP model detergents

| Component | MGDA model detergent | STPP model detergent |
|---|---|---|
| MGDA (40% solution) | 1.67 g/l | |
| STPP | | 1.65 g/l |
| Sodium carbonate | 0.66 g/l | 0.66 g/l |
| Sodium percarbonate (Dream) | 0.33 g/l | 0.33 g/l |
| Sodium disilicate | 0.17 g/l | 0.17 g/l |
| TAED (Dream) | 0.10 g/l | 0.10 g/l |
| Sokalan CP5 (39.5%) | 0.42 g/l | 0.42 g/l |
| Surfac 23-6.5 (100%) | 0.17 g/l | 0.17 g/l |
| Sodium sulphate | 1.06 g/l | |
| Phosphonate (tetra-sodium HEDP) | | 0.07 g/l |
| $CaCl_2$ | 3 mM | 3 mM |
| $MgCl_2$ | 0.75 mM | 0.75 mM |
| $NaHCO_3$ | 7.5 mM | 7.5 mM |
| pH | 10.0 | 10.0 |

Both detergents are dissolved in 50 mM CHES buffer (N-Cyclohexyl-2-aminoethanesulfonic acid, Sigma C2885) to ensure that pH is maintained during the experiment at 10.0 also after addition of protease sample.

Protease culture supernatants are pre-diluted 2-4 times and purified protease samples are diluted to approximately 0.1 and 0.05 mg/ml using deionized water. 10 μl diluted protease sample is then mixed with 190 μl model detergent solution in a well of a 0.2 ml 96-well PCR plate. After mixing, 20 μl is transferred to a 96-well microtiter plate (Nunc F) and initial protease activity is measured by adding 100 μl Suc-AAPF-pNA substrate solution (0.72 mg/ml Suc-Ala-Ala-Pro-Phe-pNA (Bachem L-1400) in 0.1 M Tris, pH 8.6) to each well, mixing and measuring absorbance at 405 nm every 20 s for 5 min on a SpectraMax Plus (Molecular Devices). Slope from linear regression on initial absorbance measurements is used for activity calculations.

The proteases in the PCR plate are then stressed by 30 min incubation at 58° C. for STPP model detergent and 60 or 62° C. for MGDA model detergent in a BioRad T100 Thermal Cycler. After rapid cooling to room temperature, 20 μl is transferred to a 96 well microtiter plate and residual activity is measured as described for the initial protease activity. The temperatures in the stress step are chosen to give suitable residual activities of the Savinase reference (polypeptide of SEQ ID NO 19) and the polypeptides (preferably in the interval 10 to 80% of the initial activity).

The decrease in activity during the stress step is assumed to be exponential. Thus, the half-life during the stress step is calculated using the formula:

$$T½=T*\ln(2)/\ln(A(\text{Initial})/A(\text{Residual}))$$

where T½ is the half-life, T is the incubation time (30 min), A(Initial) is the initial protease activity, and A(Residual) is the protease activity after the stress step. All protease samples are tested twice (using 2 times the same sample dilution for culture supernatants and 0.1 and 0.05 mg/ml for purified protease samples). Relative in wash stability improvement factor is then calculated by:

$$\text{Relative In Wash Stability Improvement Factor}=\text{Avg}(T½(\text{Sample}))/\text{Avg}(T½(\text{Reference}))$$

where Avg(T½(Samples)) is the average of the half-lifes for the given protease sample and Avg(T½(Reference)) is the average of the half-lifes for the Savinase reference sample (SEQ ID NO 19).

The results show that the proteases with SEQ ID NO 4, 6, 8 and 10 are more stable than Savinase (SEQ ID NO 19).

TABLE 3

In Wash Stability Data using MGDA and STPP model detergents

| | Relative Half Life (T½) | |
|---|---|---|
| Polypeptides | STPP | MGDA |
| SEQ ID NO 10 | 3.08 | 2.93 |
| SEQ ID NO 8 | 2.60 | 1.60 |

TABLE 3-continued

| In Wash Stability Data using MGDA and STPP model detergents | | |
|---|---|---|
| | Relative Half Life (T½) | |
| Polypeptides | STPP | MGDA |
| SEQ ID NO 6 | 1.92 | 1.13 |
| SEQ ID NO 4 | 1.44 | 0.97 |

Example 5: Wash Performance in Automatic Mechanical Stress Assay (AMSA) for Automatic Dish Wash Washing experiments are performed in order to assess the wash performance of selected protease polypeptides in dish wash detergent compositions. The proteases of the present application are tested using the Automatic Mechanical Stress Assay (AMSA). With the AMSA, the wash performance of many small volume enzyme-detergent solutions can be examined. The AMSA plate has a number of slots for test solutions and a lid that firmly squeezes the melamine tile to be washed against the slot openings. During the wash, the plate, test solutions, melamine tile and lid are vigorously shaken to bring the test solution in contact with the soiled melamine tile and apply mechanical stress in a regular, periodic oscillating manner. For further description see WO 02/42740 especially the paragraph "Special method embodiments" at page 23-24.

The experiment is conducted under the experimental conditions as specified in tables 4 and 5 below.

TABLE 4

| AMSA Experimental Conditions using ADW model detergent with MGDA | |
|---|---|
| ADW model detergent with MGDA | As defined in table 2 |
| Detergent dosage | 3.33 g/L |
| Test solution volume | 160 micro L |
| pH | 10.0 |
| Wash time | 20 minutes |
| Temperature | 45° C. |
| Water hardness | 21° dH |
| Enzyme concentration in test solution | 5.3, 10.7 mg enzyme protein/liter |
| Test material | Egg yolk melamine tile (DM-21) |

TABLE 5

| AMSA Experimental Conditions using ADW model detergent with STPP | |
|---|---|
| ADW model detergent with STPP | As defined in table 2 |
| Detergent dosage | 3.33 g/L |
| Test solution volume | 160 micro L |
| pH | 10.0 |
| Wash time | 20 minutes |
| Temperature | 45° C. |
| Water hardness | 21° dH |
| Enzyme concentration in test solution | 5.3, 10.7 mg enzyme protein/liter |
| Test material | Egg yolk melamine tile (DM-21) |

Water hardness is adjusted to 21° dH by addition of $CaCl_2$, $MgCl_2$, and $NaHCO_3$ ($Ca^{2+}$:$Mg^{2+}$:$CO_3^{2-}$=4:1:10) to the test system. After washing the egg yolk melamine tiles are flushed in tap water and dried.

The performance of the enzyme variant is measured as the brightness of the colour of the melamine tile washed with that specific protease. Brightness can also be expressed as the intensity of the light reflected from the sample when illuminated with white light. When the sample is stained the intensity of the reflected light is lower, than that of a clean sample. Therefore the intensity of the reflected light can be used to measure wash performance of a protease. Color measurements were made with a professional flatbed scanner (EPSON EXPRESSION 10000XL, Atea NS, Lautrupvang 6, 2750 Ballerup, Denmark), which is used to capture an image of the washed melamine tiles.

To extract a value for the light intensity from the scanned images, 24-bit pixel values from the image are converted into values for red, green and blue (RGB). The intensity value (Int) is calculated by adding the RGB values together as vectors and then taking the length of the resulting vector:

$$Int=\sqrt{r^2+g^2+b^2}.$$

Stains

Standard egg yolk melamine tiles (DM-21) were obtained from Center For Testmaterials BV, P.O. Box 120, 3133 KT Vlaardingen, the Netherlands.

The results are shown in table 6 below. The proteases with SEQ ID NO 4, 6 and 12 have improved was performance in dish wash compared to the protease with SEQ ID NO 19.

TABLE 6

| | Relative Performance AMSA | |
|---|---|---|
| Polypepitdes | STPP | MGDA |
| SEQ ID NO 6 | 1.1 | 1.4 |
| SEQ ID NO 4 | 1.2 | 1.1 |
| SEQ ID NO 12 | 1.1 | 1.0 |

Example 6: Wash Performance Evaluation of SEQ ID NO 2 and SEQ ID NO 4 in Powder Laundry Detergent The proteases with SEQ ID NO 2 and 4 were investigated in full scale wash. Wash performance was tested in powder model detergent with percarbonate/TEAD and compared to the known laundry protease Savinase (SEQ ID NO 19). The results are shown in Table 9.

Wash performance was evaluated using the bleach containing laundry powder model detergent as defined in table 7 below and the experimental conditions defined in table 8.

TABLE 7

| Composition of Model detergent T (powder) wt % | |
|---|---|
| LAS, sodium salt | 10.0 |
| AS, sodium salt | 1.8 |
| Soap, sodium salt | 2.0 |
| AEO | 3.0 |
| Soda ash | 14.9 |
| Hydrous sodium silicate | 2.5 |
| Zeolite A | 15.0 |
| HEDP-Na4 | 0.13 |
| Sodium citrate | 2.0 |
| PCA, copoly(acrylic acid/maleic acid), sodium salt | 1.5 |
| SRP | 0.5 |
| Sodium sulfate | 13.4 |
| Sodium percarbonate | 20.0 |
| TAED | 3.0 |
| Foam regulator | 1.0 |

CMC is added separately at 1.28 g/wash (around 13 L water intake)

TABLE 8

| Experimental condition for FSW | |
|---|---|
| Machine | Miele Softtronic W2245 FLA |
| FSW Method | EU standard wash |
| Detergent | Model powder detergent with bleach (see table 5) |
| Detergent conc. | 80 g Model T + 1.28 g CMC |
| Temperature | 40° C. |
| Enzyme dosages | 30 nM (0.10 wt % of SEQ ID NO 2 and 0.12 wt % of SEQ ID NO 4)<br>60 nM (0.20 wt % of SEQ ID NO 2 and 0.24 wt % of SEQ ID NO 4)<br>720 nM (2.38 wt % of SEQ ID NO 2 and 2.94 wt % of SEQ ID NO 4) |
| Water hardness | 15° dH (Ca/Mg/HCO3 = 4:1:7.5) |
| Wash time | 41 min main wash |
| Enzymes | Savinase (SEQ ID NO 19), SEQ ID NO 2 and SEQ ID NO 4 |
| Stain/swatch | C-05 Blood/milk/ink<br>CS-01 Aged blood |
| Ballast | 3 kg mixed cotton/polyester (ratio 65:35) |
| Soil ballast | 2 pieces SBL2004 and other enzyme sensitive stains like PC-03 (Chocolate milk/soot), C-H097 (Oatmeal/Chocolate) EMPA 112 (Cocoa), C-H010 (Cocoa cocked up with milk), CS-44 (Chocolate drink), WFK 10Z (Chocolate), CS-37 (Full egg/ Pigment), WFK10N (Whole Egg), WFK10EG (Egg Yolk), 051KC (Egg), EMPA 164 (Grass), 062KC (Scrubbed Grass), WE5GMWKC (Grass/Mud), C-10 (Milk/Oil/Pigment) C-H165 (Minced meat) and KH-H172 (Meat Pate) |

Test materials, were obtained from Center For Testmaterials BV, P.O. Box 120, 3133 KT Vlaardingen, the Netherlands, SBL2004 and the other enzyme sensitive stains were obtained either from Center For Testmaterials BV, P.O. Box 120, 3133 KT Vlaardingen, the Netherlands, or EMPA Testmaterials AG, Möwenstrasse 12, CH-9015 St. Gallen, Switzerland or WFK Testgewebe GmbH, Christenfeld 10, D-41379 Brüggen, Germany.

Wash performance was measured as delta remission on swatches, which after wash were dried overnight on tray (12 h-20 h) at room (around 20-25 C) temperature and 40% humidity, then measured at 460 nm in Coloreye equipment stacked 2 pieces in the second day.

Table 9 shows the performance as delta remission of the proteases with SEQ ID NO 2 and 4 on two different types of blood stains.

TABLE 9

| | 30 nM | | 60 nM | | 720 nM | |
|---|---|---|---|---|---|---|
| Polypeptides | SEQ ID NO 2 | SEQ ID NO 4 | SEQ ID NO 2 | SEQ ID NO 4 | SEQ ID NO 2 | SEQ ID NO 4 |
| Heat treated C-05 Blood/milk/ink | 4.16 | 4.25 | 4.05 | 4.63 | 2.93 | 3.40 |
| CS-01 Aged blood | 3.46 | 5.39 | 5.30 | 7.29 | 8.98 | 12.94 |

The data clearly show an improved wash performance of protease with SEQ NO 2 and SEQ NO 4 relative to Savinase (SEQ ID NO 19) on the aged/heat treated blood stains C-05 and CS-01.

Example 7: Performance of Polypeptides on Blood Stains

Detergent Model X pH Profile (on EMPA117EH)

The assay was performed in a 96 well microtiter plate 96 with two EMPA117 EH (blood/milk/ink extra heated) swatches and the measurement performed in a 384 well microtiter plate.

| | | |
|---|---|---|
| Model detergent X | LAS | 17.6 wt % |
| | AEO* | 2.0 wt % |
| | Sodium carbonate | 20.1 wt % |
| | Hydrous sodium silicate | 12.4 wt % |
| | Zeolite A | 15.0 wt % |
| | Sodium sulfate | 31.8 wt % |
| | Polyacrylate | 1.1 wt % |

*AEO is added separately 100 ml Detergent:

0.2 g Model X

233 μl 0.713M $CaCl_2$

233 μl 0.357M $MgCl_2$

700 μl 0.535M $NaHCO_3$ 80 ml Multibuffer 50 mM pH 8-11

10 μl of purified polypeptide normalized to a concentration of 10 μM (μmol/Liter) in Buffer: 20 mM MES; 0.01% Triton 100-X; 2 mM $CaCl_2$ was diluted MilliQ/0.01% Triton 2000 times for a final concentration of 5 nM. The polypeptides were tested on the EMPA117 EH swatch. 96 well microtiter plates were shaken 1000 rpm for 30 min. Aspirate 50 μl from the 96 well microtiter plates to clear 384 well microtiter plates and measure OD590 endpoint. Improvement factor is the measured endpoint value for the variant divided by the measured endpoint value for the reference enzyme (SEQ ID NO 19).

Table 10 shows the performance (improvement factor (IF) compared to the polypeptide with SEQ ID NO 19 with IF=1) of the polypeptides in the assay described above at pH 8 and/or pH 9, pH 10 and pH 11 on the stain EMPA117EH (blood/milk/ink extra heated).

TABLE 10

| Protease SEQ ID NO | pH 8 | pH 9 | pH 10 | pH 11 |
|---|---|---|---|---|
| SEQ ID NO 4 | 1.4 | 1.8 | 1.7 | 1.3 |
| SEQ ID NO 10 | 1.6 | 1.4 | 1.4 | 1.3 |
| SEQ ID NO 12 | 1.3 | 1.3 | 1.3 | 1.3 |
| SEQ ID NO 14 | 1.3 | 1.4 | 1.4 | 1.2 |
| SEQ ID NO 16 | 1.4 | 1.2 | 1.6 | 1.2 |
| SEQ ID NO 18 | 1.7 | 2.3 | 2.0 | 2.3 |

The tested polypeptides with SEQ ID NO 4, 10, 12, 14, 16 and 18 show improved performance on the blood stain EMPA117 EH Blood/milk/ink on cotton/polyester at four different pH values.

AZCL-Hemoglobin Assay:

Substrate: "AZCL-Hemoglobin" (Megazyme) substrate based on a Azurine-crosslinking to the hemoglobin molecule.

The assay is performed in 96 well microtiter plates with AZCL-hemoglobin substrate and the measurement is performed in a 384 well microtiter plates. 10 μl of purified polypeptide normalized to a concentration of 10 μM (μmol/Liter) in Buffer: 20 mM MES; 0.01% Triton 100-X; 2 mM $CaCl_2$ was mixed with 90 μl 0.01% Triton 100X and 5 μl of this solution was mixed with 195 μl Substrate mix (AZCL-Hemoglobin 10 mg/ml in Multibuffer). The 96 well microtiter plates were shaken 1000 rpm for 30 min. Aspirate 50 μl from the 96 well microtiter plates to clear 384 well microtiter plates and measure OD590 endpoint. Improvement factor is the measured endpoint value for the variant divided by the measured endpoint value for the reference enzyme (SEQ ID NO 3). Table 11 show the performance of the protease variants in the assay described above at pH 8 and/or pH 9, pH 10 and pH 11 on AZCL-Hemoglobin" (Megazyme).

TABLE 11

| protease SEQ ID NO | pH 8 | pH 9 | pH 10 | pH 11 |
|---|---|---|---|---|
| SEQ ID NO 4 | 1.3 | 2.9 | 3.2 | 1.9 |
| SEQ ID NO 12 | 1.9 | 2.3 | 2.5 | 1.6 |
| SEQ ID NO 14 | 1.2 | 1.1 | 1.1 | |
| SEQ ID NO 16 | 1.6 | 2.7 | 3.2 | 1.8 |

The tested polypeptides with SEQ ID NO 4, 12, 14 and 16 show improved performance on the blood stain AZCL-Hemoglobin" (Megazyme) at four different pH values.

The invention claimed is:

1. A detergent composition suitable for laundry or dishwashing comprising at least one detergent component and an active protease, wherein the protease is a polypeptide comprising SEQ ID NO 4.

2. The composition of claim 1, wherein said composition is a dishwashing composition comprising:

a) at least 0.01 mg of active protease per gram of composition, wherein the protease is a polypeptide comprising SEQ ID NO 4, b) at least one builder, and c) at least one bleach component.

3. The dishwashing composition of claim 2, wherein the dishwashing composition is an automatic dish wash (ADW) composition or a hand dishwash (HD) composition.

4. The dishwashing composition according to claim 2, wherein the builder is selected from the group consisting of phosphates, sodium citrate builders, sodium carbonate, sodium silicate, and sodium zeolites.

5. The dishwashing composition according to claim 2, comprising about 10-65% by weight of at least one builder.

6. The dishwashing composition according to claim 2, comprising 5-50% by weight of a detergent co-builder.

7. The dishwashing composition according to claim 2, wherein the composition is phosphate free.

8. The dishwashing composition according to claim 2, wherein the builder is selected from the group consisting of citric acid, methyl glycine-N,N-diacetic acid (MGDA) glutamic-N,N-diacetic acid (GLDA) and mixtures thereof.

9. The dishwashing composition according to claim 2, wherein the bleach component is selected from the group consisting of bleaching catalysts, photobleaches, bleach activators, sources of hydrogen peroxide, preformed peracids and mixtures thereof.

10. The dishwashing composition according to claim 2, wherein the bleach component is a peroxide selected from the group consisting of percarbonate, persulfate, perphosphate, and persilicate salts.

11. The dishwashing composition according to claim 2, wherein the bleaching component includes a percarbonate and a bleach catalyst.

12. The dishwashing composition of claim 11, wherein the bleach catalyst is 1,4,7-trimethyl-1,4,7-triazacyclononane or manganese (II) acetate tetrahydrate (Mn-TACN).

13. The dishwashing composition according to claim 2, comprising from 1-40 wt % of bleaching components, wherein the bleach components are a peroxide and a catalyst.

14. The composition of claim 1, wherein said composition is a granular detergent composition comprising:

a) at least 0.01 mg of active protease per gram of composition, wherein the protease is a polypeptide comprising SEQ ID NO 4, b) 5 wt % to 50 wt % anionic surfactant, c) 1 wt % to 8 wt % nonionic surfactant, and d) 5 wt % to 40 wt % of at least one builder.

15. The granular detergent composition of claim 14, wherein the anion surfactant is selected from the group consisting of linear alkylbenzenesulfonates (LAS), isomers of LAS, alcohol ether sulfate (AEOS), sodium lauryl ether sulfate, and sodium laureth sulfate (SLES).

16. The granular detergent composition of claim 14, wherein the nonionic surfactant is selected from the group consisting of primary alcohol ethoxylates and alkyl ester sulphates.

17. The granular detergent composition according to claim 14, wherein the builder is a carbonates, or a zeolites builder.

18. The granular detergent composition according to claim 14, wherein the builder is selected from the group consisting of citric acid, methyl glycine-N,N-diacetic acid (MGDA) glutamic-N,N-diacetic acid (GLDA) and mixtures thereof.

19. The granular detergent composition according to claim 14, which additionally comprises a peroxide bleach component selected from the group consisting of percarbonate, persulfate, perphosphate, and persilicate salts.

20. The composition of claim 1, wherein said composition is a detergent composition comprising:

a) at least 0.01 mg of active protease per gram detergent, wherein the protease is a polypeptide comprising SEQ ID NO 4, b) 2 wt % to 60 wt % of at least one surfactant, and c) 5 wt % to 50 wt % of at least one builder.

21. The detergent composition of claim 20, wherein said detergent composition is a liquid or powder laundry detergent composition.

22. The detergent composition of claim 20, wherein the surfactant is selected from the group consisting of: nonionic, anionic and amphoteric surfactants.

23. The composition of claim 1, wherein said polypeptide consists of the amino acid sequence of SEQ ID NO 4.

24. A method for removing a stain from a surface, the method comprising contacting the surface with the composition according to claim 1.

25. The dishwashing composition of claim 13, wherein the catalyst is 1,4,7-trimethyl-1,4,7-triazacyclononane, manganese (II) acetate tetrahydrate (MnTACN), or another metal-containing bleach catalyst.

26. The dishwashing composition of claim 9, wherein the sources of hydrogen peroxide are selected from the group consisting of sodium percarbonate, sodium perborates and hydrogen peroxide.

* * * * *

SEQUENCE LISTING

```
<160> NUMBER OF SEQ ID NOS: 19

<210> SEQ ID NO 1
<211> LENGTH: 1143
<212> TYPE: DNA
<213> ORGANISM: Artificial Sequence
<220> FEATURE:
<223> OTHER INFORMATION: Artificial DNA1

<400> SEQUENCE: 1

atgaagaaac cgttggggaa aattgtcgca agcaccgcac tactcatttc tgttgctttt     60

agttcatcga tcgcatcggc tgctgaagaa gcaaaagaaa aatatttaat tggctttaat    120

gagcaggaag ctgtcagtga gtttgtagaa caagtagagg caaatgacga ggtcgccatt    180

ctctctgagg aagaggaagt cgaaattgaa ttgcttcatg aatttgaaac gattcctgtt    240

ttatccgttg agttaagccc agaagatgtg gacgcgcttg aactcgatcc agcgatttct    300

tatattgaag aggatgcaga agtaacgaca atggcgcaat cggtaccatg gggaattcgc    360

cgtgtgcaag ccccaactgc ccataaccgt ggattgacag gttctggtgt aaaagttgct    420

gtcctcgata cagggatatc cactcatcca gatctaaata ttcgtggtgg cgcaagcttt    480

gtaccagggg aaccgtcgac tcaagatggg aatgggcatg gcacgcatgc ggccgggacg    540

atcgctgctt taaacaattc gattggcgtt cttggcgtag ctcctagcgc tgagctatac    600

gctgttaaag tcctaggggc gagcggttca ggttcggtca gctcgattgc ccaaggattg    660

gaatgggcag ggaacaatgg catgcacgtt gctaatttga gtttaggaag cccttcgcca    720

agtgccacac tcgagcaagc tgttaatagc gcgacttcta gaggcgttct tgttgtagcg    780

gcatctggga attcaggtgc aggctcaatc agctatccgg cgcgctatgc gaacgcaatg    840

gcagtcggag ctactgatca aaacaacaac cgcgctagct tttcacagta tggcgcaggc    900

cttgacattg tcgcacccgg ggtaaacgtg cagagcacat acccaggttc aacatatgcc    960

agcttggacg gtacatctat ggctactcct catgttgcag gtgcggccgc ccttgttaaa   1020

caaaagaacc catcttggtc taatgtacgt attcgaaatc atctaaagaa tacggcaact   1080

agtttaggaa gcacgaactt gtatggaagc ggacttgtta acgcagaagc ggcaacgcgt   1140

taa                                                                  1143


<210> SEQ ID NO 2
<211> LENGTH: 269
<212> TYPE: PRT
<213> ORGANISM: Artificial
<220> FEATURE:
<223> OTHER INFORMATION: Polypeptide 2

<400> SEQUENCE: 2

Ala Gln Ser Val Pro Trp Gly Ile Arg Arg Val Gln Ala Pro Thr Ala
```

-continued

```
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Ala Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asp Gly Thr Ser Met Ala Thr Pro His Val Ala Gly Ala
    210                 215                 220

Ala Ala Leu Val Lys Gln Lys Asn Pro Ser Trp Ser Asn Val Arg Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

<210> SEQ ID NO 3
<211> LENGTH: 1143
<212> TYPE: DNA
<213> ORGANISM: Artificial
<220> FEATURE:
<223> OTHER INFORMATION: Artificial DNA3

<400> SEQUENCE: 3

```
atgaaaaaac cgctggggaa aattgtcgca agcaccgcac tactcatttc tgttgctttt      60

agttcatcga tcgcatcggc tgctgaagaa gcaaaagaaa aatatttaat tggctttaat     120

gagcaggaag ctgtcagtga gtttgtagaa caagtagagg caaatgacga ggtcgccatt     180

ctctctgagg aagaggaagt cgaaattgaa ttgcttcatg aatttgaaac gattcctgtt     240

ttatccgttg agttaagccc agaagatgtg gacgcgcttg aactcgatcc agcgatttct     300

tatattgaag aggatgcaga agtaacgaca atggcgcaat cggtaccatg gggaattcgc     360

cgtgtgcaag ccccaactgc ccataaccgt ggattgacag gttctggtgt aaaagttgct     420

gtcctcgata cagggatatc cactcatcca gatctaaata ttcgtggtgg cgcaagcttt     480

gtaccagggg aaccgtcgac tcaagatgaa aatgggcatg gcacgcatgc ggccgggacg     540

atcgctgctt taaacaattc gattggcgtt cttggcgtag ctcctagcgc tgagctatac     600
```

-continued

```
gctgttaaag tcctaggagc aagcggttca ggttcggtca gctcgattgc ccaaggattg    660

gaatgggcag ggaacaatgg catgcacgtt gctaatttga gtttaggaag cccttcgcca    720

agtgccacac tcgagcaagc tgttaatagc gcgacttcta gaggcgttct tgttgtagcg    780

gcatctggga attcaggtgc aggctcaatc agctatccgg cgcgctatgc gaacgcaatg    840

gcagtcggag ctactgatca aaacaacaac cgcgctagct tttcacagta tggcccaggc    900

cttgacattg tcgcacccgg ggtaaacatt cagagcacat acccaggttc aacatatgcc    960

agcttgaacg gtacatcgat ggctactcct catgttgcag gtgcggccgc ccttgttaaa   1020

caaaagaacc catcttggtc taatgtacgt attcgaaatc atctaaagaa tacggcaact   1080

agtttaggaa gcacggactt gtatggaagc ggacttgtta acgcagaagc ggcaacgcgt   1140

taa                                                                 1143


<210> SEQ ID NO 4
<211> LENGTH: 269
<212> TYPE: PRT
<213> ORGANISM: Artificial
<220> FEATURE:
<223> OTHER INFORMATION: Polypeptide 4

<400> SEQUENCE: 4

Ala Gln Ser Val Pro Trp Gly Ile Arg Arg Val Gln Ala Pro Thr Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Glu Asn Gly His Gly Thr
    50                  55                  60

His Ala Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Pro Gly Leu Asp Ile
            180                 185                 190

Val Ala Pro Gly Val Asn Ile Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Arg Ile
225                 230                 235                 240

Arg Asn His Leu Lys Asn Thr Ala Thr Ser Leu Gly Ser Thr Asp Leu
                245                 250                 255
```

-continued

```
Tyr Gly Ser Gly Leu Val Asn Ala Glu Ala Ala Thr Arg
            260                 265


<210> SEQ ID NO 5
<211> LENGTH: 1140
<212> TYPE: DNA
<213> ORGANISM: Artificial
<220> FEATURE:
<223> OTHER INFORMATION: Artificial DNA5

<400> SEQUENCE: 5

atgaaaaaac cgctggggaa aattgtcgca agcaccgcac tactcatttc tgttgctttt     60

agttcatcga tcgcatcggc tgctgaagaa gcaaaagaaa aatatttaat tggctttaat    120

gagcaggaag ctgtcagtga gtttgtagaa caagtagagg caaatgacga ggtcgccatt    180

ctctctgagg aagaggaagt cgaaattgaa ttgcttcatg aatttgaaac gattcctgtt    240

ttatccgttg agttaagccc agaagatgtg gacgcgcttg aactcgatcc agcgatttct    300

tatattgaag aggatgcaga agtaacgaca atggcgcaat cggtaccatg gggaattaga    360

cgtgtgcaag ccccaactgc ccataaccgt ggattgacag gttctggtgt aaaagttgct    420

gtcctcgata cagggatatc cactcatcca gatctaaata ttcgtggtgg cgcaagcttt    480

gtaccagggg aaccgtcgac tcaagatggg aatgggcatg gcacgcatgt ggccgggacg    540

atcgctgctt taaacaattc gattggcgtt cttggcgtag ctcctagcgc tgagctatac    600

gctgttaaag tcctaggggc gagcggttca ggttcggtca gctcgattgc ccaaggattg    660

gaatgggcag ggaacaatgg catgaatgtt gctaatttga gtttaggaag cccttcgagt    720

gccacactcg agcaggctgt taatagcgcg acttctagag gcgttcttgt tgtagcggca    780

tctgggaatt caggtgcagg ctcaatcagc tatccggcgc gctatgcgaa cgcaatggca    840

gtcggagcta ctgatcaaaa caacaaccgc gctagctttt cacagtatgg cgcaggcctt    900

gacattgtcg cacccggggt aaacgtggaa agcacatacc caggttcaac gtatgccagc    960

ttgaacggta catcgatggc tactcctcat gttgcaggtg cggccgccct tgttaaacaa   1020

aagaacccat cttggtctaa tgtacaaatt cgaaatcatc taaagaatac ggcaactagt   1080

ttaggaagca cgaacttgta tggaagcgga cttgttaacg cagaagcggc aacgcgttaa   1140


<210> SEQ ID NO 6
<211> LENGTH: 268
<212> TYPE: PRT
<213> ORGANISM: Artificial
<220> FEATURE:
<223> OTHER INFORMATION: Artificial polypeptide 6

<400> SEQUENCE: 6

Ala Gln Ser Val Pro Trp Gly Ile Arg Arg Val Gln Ala Pro Thr Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95
```

-continued

```
Ser Gly Ser Gly Ser Val Ser Ser Ile Ala Gln Gly Leu Glu Trp Ala
            100                 105                 110

Gly Asn Asn Gly Met Asn Val Ala Asn Leu Ser Leu Gly Ser Pro Ser
        115                 120                 125

Ser Ala Thr Leu Glu Gln Ala Val Asn Ser Ala Thr Ser Arg Gly Val
    130                 135                 140

Leu Val Val Ala Ala Ser Gly Asn Ser Gly Ala Gly Ser Ile Ser Tyr
145                 150                 155                 160

Pro Ala Arg Tyr Ala Asn Ala Met Ala Val Gly Ala Thr Asp Gln Asn
                165                 170                 175

Asn Asn Arg Ala Ser Phe Ser Gln Tyr Gly Ala Gly Leu Asp Ile Val
            180                 185                 190

Ala Pro Gly Val Asn Val Glu Ser Thr Tyr Pro Gly Ser Thr Tyr Ala
        195                 200                 205

Ser Leu Asn Gly Thr Ser Met Ala Thr Pro His Val Ala Gly Ala Ala
    210                 215                 220

Ala Leu Val Lys Gln Lys Asn Pro Ser Trp Ser Asn Val Gln Ile Arg
225                 230                 235                 240

Asn His Leu Lys Asn Thr Ala Thr Ser Leu Gly Ser Thr Asn Leu Tyr
                245                 250                 255

Gly Ser Gly Leu Val Asn Ala Glu Ala Ala Thr Arg
            260                 265
```

<210> SEQ ID NO 7
<211> LENGTH: 1140
<212> TYPE: DNA
<213> ORGANISM: Artificial
<220> FEATURE:
<223> OTHER INFORMATION: Artificial DNA 7

<400> SEQUENCE: 7

```
atgaaaaaac cgctggggaa aattgtcgca agcaccgcac tactcatttc tgttgctttt     60

agttcatcga tcgcatcggc tgctgaagaa gcaaaagaaa aatatttaat tggctttaat    120

gagcaggaag ctgtcagtga gtttgtagaa caagtagagg caaatgacga ggtcgccatt    180

ctctctgagg aagaggaagt cgaaattgaa ttgcttcatg aatttgaaac gattcctgtt    240

ttatccgttg agttaagccc agaagatgtg gacgcgcttg aactcgatcc agcgatttct    300

tatattgaag aggatgcaga agtaacgaca atggcgcaag ttgtaccatg gggaattaga    360

cgtgtgcaag ccccaactgc ccataaccgt ggattgacag gttctggtgt aaaagttgct    420

gtcctcgata cagggatatc cactcatcca gatctaaata ttcgtggtgg cgcaagcttt    480

gtaccagggg aaccgtcgac tcaagatggg aatgggcatg gcacgcatgt ggccgggacg    540

atcgctgctt taaacaattc gattggcgtt cttggcgtag ctcctagcgc tgagctatac    600

gctgttaaag tcctaggggc gagcggttca ggttcggtca gctcgattgc ccaaggattg    660

gaatgggcag ggaacaatgg catgaatgtt gctaatttga gtttaggaag cccttcgagt    720

gccacactcg agcaggctgt taatagcgcg acttctagag gcgttcttgt tgtagcggca    780

tctgggaatt caggtgcagg ctcaatcagc tatccggcgc gctatgcgaa cgcaatggca    840

gtcggagcta ctgatcaaaa caacaaccgc gctagctttt cacagtatgg cgcaggcctt    900

gacattgtcg cacccggggt aaacgtgcag agcacatacc caggttcaac gtatgccagc    960

ttgaacggta catcgatggc tactcctcat gttgcaggtg cggccgccct tgttaaacaa   1020

aagaacccat cttggtctaa tgtacaaatt cgaaatcatc taaagaatac ggcaactagt   1080
```

ttaggaagca cgaacttgta tggaagcgga cttgttaacg cagaagcggc aacgcgttaa 1140

<210> SEQ ID NO 8
<211> LENGTH: 268
<212> TYPE: PRT
<213> ORGANISM: Artificial
<220> FEATURE:
<223> OTHER INFORMATION: Polypeptide 8

<400> SEQUENCE: 8

Ala Gln Val Val Pro Trp Gly Ile Arg Arg Val Gln Ala Pro Thr Ala
1 5 10 15

His Asn Arg Gly Leu Thr Gly Ser Gly Val Lys Val Ala Val Leu Asp
20 25 30

Thr Gly Ile Ser Thr His Pro Asp Leu Asn Ile Arg Gly Gly Ala Ser
35 40 45

Phe Val Pro Gly Glu Pro Ser Thr Gln Asp Gly Asn Gly His Gly Thr
50 55 60

His Val Ala Gly Thr Ile Ala Ala Leu Asn Asn Ser Ile Gly Val Leu
65 70 75 80

Gly Val Ala Pro Ser Ala Glu Leu Tyr Ala Val Lys Val Leu Gly Ala
85 90 95

Ser Gly Ser Gly Ser Val Ser Ser Ile Ala Gln Gly Leu Glu Trp Ala
100 105 110

Gly Asn Asn Gly Met Asn Val Ala Asn Leu Ser Leu Gly Ser Pro Ser
115 120 125

Ser Ala Thr Leu Glu Gln Ala Val Asn Ser Ala Thr Ser Arg Gly Val
130 135 140

Leu Val Val Ala Ala Ser Gly Asn Ser Gly Ala Gly Ser Ile Ser Tyr
145 150 155 160

Pro Ala Arg Tyr Ala Asn Ala Met Ala Val Gly Ala Thr Asp Gln Asn
165 170 175

Asn Asn Arg Ala Ser Phe Ser Gln Tyr Gly Ala Gly Leu Asp Ile Val
180 185 190

Ala Pro Gly Val Asn Val Gln Ser Thr Tyr Pro Gly Ser Thr Tyr Ala
195 200 205

Ser Leu Asn Gly Thr Ser Met Ala Thr Pro His Val Ala Gly Ala Ala
210 215 220

Ala Leu Val Lys Gln Lys Asn Pro Ser Trp Ser Asn Val Gln Ile Arg
225 230 235 240

Asn His Leu Lys Asn Thr Ala Thr Ser Leu Gly Ser Thr Asn Leu Tyr
245 250 255

Gly Ser Gly Leu Val Asn Ala Glu Ala Ala Thr Arg
260 265

<210> SEQ ID NO 9
<211> LENGTH: 1143
<212> TYPE: DNA
<213> ORGANISM: Artificial
<220> FEATURE:
<223> OTHER INFORMATION: Artificial DNA 9

<400> SEQUENCE: 9
atgaaaaaac cgctggggaa aattgtcgca agcaccgcac tactcatttc tgttgctttt 60
agttcatcga tcgcatcggc tgctgaagaa gcaaaagaaa aatatttaat tggctttaat 120
gagcaggaag ctgtcagtga gtttgtagaa caagtagagg caaatgacga ggtcgccatt 180

```
ctctctgagg aagaggaagt cgaaattgaa ttgcttcatg aatttgaaac gattcctgtt    240
ttatccgttg agttaagccc agaagatgtg gacgcgcttg aactcgatcc agcgatttct    300
tatattgaag aggatgcaga agtaacgaca atggcgcaag ttgtaccatg ggaattcgc    360
cgtgtgcaag ccccaactgc ccataaccgt ggattgacag gttctggtgt aaaagttgct    420
gtcctcgata cagggatatc cactcatcca gatctaaata ttcgtggtgg cgcaagcttt    480
gtaccagggg aaccgtcgac tcaagatgaa aatgggcatg gcacgcatgc ggccgggacg    540
atcgctgctt taaacaattc gattggcgtt cttggcgtag ctcctagcgc tgagctatac    600
gctgttaaag tcctaggagc aagcggttca ggttcggtca gctcgattgc ccaaggattg    660
gaatgggcag ggaacaatgg catgcacgtt gctaatttga gtttaggaag cccttcgcca    720
agtgccacac tcgagcaagc tgttaatagc gcgacttcta gaggcgttct tgttgtagcg    780
gcatctggga attcaggtgc aggctcaatc agctatccgg cgcgctatgc gaacgcaatg    840
gcagtcggag ctactgatca aaacaacaac cgcgctagct tttcacagta tggcccaggc    900
cttgacattg tcgcacccgg ggtaaacatt cagagcacat acccaggttc aacatatgcc    960
agcttgaacg gtacatcgat ggctactcct catgttgcag gtgcggccgc ccttgttaaa   1020
caaaagaacc catcttggtc taatgtacgt attcgaaatc atctaaagaa tacggcaact   1080
agtttaggaa gcacggactt gtatggaagc ggacttgtta acgcagaagc ggcaacgcgt   1140
taa                                                                 1143
```

<210> SEQ ID NO 10
<211> LENGTH: 269
<212> TYPE: PRT
<213> ORGANISM: Artificial
<220> FEATURE:
<223> OTHER INFORMATION: Polypeptide 10

<400> SEQUENCE: 10

```
Ala Gln Val Val Pro Trp Gly Ile Arg Arg Val Gln Ala Pro Thr Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Glu Asn Gly His Gly Thr
    50                  55                  60

His Ala Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Pro Gly Leu Asp Ile
            180                 185                 190
```

Val Ala Pro Gly Val Asn Ile Gln Ser Thr Tyr Pro Gly Ser Thr Tyr
195 200 205

Ala Ser Leu Asn Gly Thr Ser Met Ala Thr Pro His Val Ala Gly Ala
210 215 220

Ala Ala Leu Val Lys Gln Lys Asn Pro Ser Trp Ser Asn Val Arg Ile
225 230 235 240

Arg Asn His Leu Lys Asn Thr Ala Thr Ser Leu Gly Ser Thr Asp Leu
245 250 255

Tyr Gly Ser Gly Leu Val Asn Ala Glu Ala Ala Thr Arg
260 265

<210> SEQ ID NO 11
<211> LENGTH: 1143
<212> TYPE: DNA
<213> ORGANISM: Artificial
<220> FEATURE:
<223> OTHER INFORMATION: Artificial DNA 11

<400> SEQUENCE: 11
atgaaaaaac cgctggggaa aattgtcgca agcaccgcac tactcatttc tgttgctttt 60
agttcatcga tcgcatcggc tgctgaagaa gcaaaagaaa aatatttaat tggctttaat 120
gagcaggaag ctgtcagtga gtttgtagaa caagtagagg caaatgacga ggtcgccatt 180
ctctctgagg aagaggaagt cgaaattgaa ttgcttcatg aatttgaaac gattcctgtt 240
ttatccgttg agttaagccc agaagatgtg gacgcgcttg aactcgatcc agcgatttct 300
tatattgaag aggatgcaga agtaacgaca atggcgcaat cggtaccatg gggaattaga 360
cgtgtgcaag ccccaactgc ccataaccgt ggattgacag gttctggtgt aaaagttgct 420
gtcctcgata cagggatatc cactcatcca gatctaaata ttcgtggtgg cgcaagcttt 480
gtaccagggg aaccgtcgac tcaagatggg aatgggcatg gcacgcatgc agccgggacg 540
atcgctgctt taaacaattc gattggcgtt cttggcgtag ctcctagcgc tgagctatac 600
gctgttaaag tcctaggagc agatggttca ggttcggtca gctcgattgc ccaaggattg 660
gaatgggcag ggaacaatgg catgaatgtt gctaatttga gtttaggaag cccttcgacg 720
agtgccacac tcgagcaggc tgttaatagc gcgacttcta gaggcgttct tgttgtagcg 780
gcatctggga attcaggtgc aggctcaatc agctatccgg cgcgctatgc gaacgcaatg 840
gcagtcggag ctactgatca aaacaacaac cgcgctagct tttcacagta tggcccaggc 900
cttgacattg tcgcacccgg ggtaaacgtg gaaagcacat acccaggttc aacatatgcc 960
agcttgaacg gtacatcgat ggctactcct catgttgcag gtgcggccgc ccttgttaaa 1020
caaaagaacc catcttggtc taatgtacaa attcgaaatc atctaaagaa tacggcaact 1080
agtttaggaa gcacgaactt gtatggaagc ggacttgtta acgcagaagc ggcaacgcgt 1140
taa 1143

<210> SEQ ID NO 12
<211> LENGTH: 269
<212> TYPE: PRT
<213> ORGANISM: Artificial
<220> FEATURE:
<223> OTHER INFORMATION: Polypeptide 12

<400> SEQUENCE: 12

Ala Gln Ser Val Pro Trp Gly Ile Arg Arg Val Gln Ala Pro Thr Ala
1 5 10 15

-continued

```
His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Ala Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Ser Gly Ser Val Ser Ser Ile Ala Gln Gly Leu Glu Trp Ala
            100                 105                 110

Gly Asn Asn Gly Met Asn Val Ala Asn Leu Ser Leu Gly Ser Pro Ser
        115                 120                 125

Thr Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Pro Gly Leu Asp Ile
            180                 185                 190

Val Ala Pro Gly Val Asn Val Glu Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

```
<210> SEQ ID NO 13
<211> LENGTH: 1143
<212> TYPE: DNA
<213> ORGANISM: Artificial
<220> FEATURE:
<223> OTHER INFORMATION: Artificial DNA 13

<400> SEQUENCE: 13

atgaaaaaac cgctggggaa aattgtcgca agcaccgcac tactcatttc tgttgctttt     60

agttcatcga tcgcatcggc tgctgaagaa gcaaaagaaa aatatttaat tggctttaat    120

gagcaggaag ctgtcagtga gtttgtagaa caagtagagg caaatgacga ggtcgccatt    180

ctctctgagg aagaggaagt cgaaattgaa ttgcttcatg aatttgaaac aattcctgtt    240

ttatccgttg agttaagccc agaagatgtg gacgcgcttg aactcgatcc agcgatttct    300

tatattgaag aggatgcaga agtaacgaca atggcgcaat cggtaccatg gggaattcgc    360

cgtgtgcaag ccccaactgc ccataaccgt ggattgacag gttctggtgt aaaagttgct    420

gtcctcgata cagggatatc cactcatcca gatctaaata ttcgtggtgg cgcaagcttt    480

gtaccagggg aaccgtcgac tcaagatggg aatgggcatg gcacgcatgc ggccgggacg    540

atcgctgctt taaacaattc gattggcgtt cttggcgtag ctcctagcgc tgagctatac    600

gctgttaaag tcctaggagc aagcggttca ggttcggtca gctcgattgc ccaaggattg    660
```

-continued

```
gaatgggcag ggaacaatgg catgcacgtt gctaatttga gtttaggaag cccttcgcca    720

agtgccacac tcgagcaagc tgttaatagc gcgacttcta gaggcgttct tgttgtagcg    780

gcatctggga attcaggtgc aggctcaatc agctatccgg cgcgctatgc gaacgcaatg    840

gcagtcggag ctactgatca aaacaacaac cgcgctagct tttcacagta tggcccaggc    900

cttgacattg tcgcacccgg ggtaaacgtg cagagcacat acccaggttc aacatatgcc    960

agcttgaacg gtacatcgat ggctactcct catgttgcag gtgcggccgc ccttgttaaa   1020

caaaagaacc catcttggtc taatgtacgt attcgaaatc atctaaagaa tacggcaact   1080

agtttaggaa gcacggacta ttatggaagc ggacttgtta acgcagaagc ggcaacgcgt   1140

taa                                                                 1143


<210> SEQ ID NO 14
<211> LENGTH: 269
<212> TYPE: PRT
<213> ORGANISM: Artificial
<220> FEATURE:
<223> OTHER INFORMATION: Polypeptide 14

<400> SEQUENCE: 14

Ala Gln Ser Val Pro Trp Gly Ile Arg Arg Val Gln Ala Pro Thr Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Ala Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Pro Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Arg Ile
225                 230                 235                 240

Arg Asn His Leu Lys Asn Thr Ala Thr Ser Leu Gly Ser Thr Asp Tyr
                245                 250                 255

Tyr Gly Ser Gly Leu Val Asn Ala Glu Ala Ala Thr Arg
            260                 265
```

<210> SEQ ID NO 15
<211> LENGTH: 1143
<212> TYPE: DNA
<213> ORGANISM: Artificial
<220> FEATURE:
<223> OTHER INFORMATION: Artificial DNA 15

<400> SEQUENCE: 15
atgaaaaaac cgctggggaa aattgtcgca agcaccgcac tactcatttc tgttgctttt 60
agttcatcga tcgcatcggc tgctgaagaa gcaaaagaaa aatatttaat tggctttaat 120
gagcaggaag ctgtcagtga gtttgtagaa caagtagagg caaatgacga ggtcgccatt 180
ctctctgagg aagaggaagt cgaaattgaa ttgcttcatg aatttgaaac gattcctgtt 240
ttatccgttg agttaagccc agaagatgtg gacgcgcttg aactcgatcc agcgatttct 300
tatattgaag aggatgcaga agtaacgaca atggcgcaag ttgtaccatg ggaattagc 360 cgtgtgcaag ccccaactgc ccataaccgt ggattgacag gttctggtgt aaaagttgct 420
gtcctcgata cagggatatc cactcatcca gatctaaata ttcgtggtgg cgcaagcttt 480
gtaccagggg aaccgtcgac tcaagatggg aatgggcatg gcacgcatgc ggccgggacg 540
atcgctgctt taaacaattc gattggcgtt cttggcgtag ctcctagcgc tgagctatac 600
gctgttaaag tcctaggagc aagcggttca ggttcggtca gctcgattgc ccaaggattg 660
gaatgggcag ggaacaatgg catgcacgtt gctaatttga gtttaggaag cccttcgcca 720
agtgccacac tcgagcaagc tgttaatagc gcgacttcta gaggcgttct tgttgtagcg 780
gcatctggga attcaggtgc aggctcaatc agctatccgg cgcgctatgc gaacgcaatg 840
gcagtcggag ctactgatca aaacaacaac cgcgctagct tttcacagta tggcccaggc 900
cttgacattg tcgcacccgg ggtaaacgtg cagagcacat acccaggttc aacatatgcc 960
agcttgaacg gtacatcgat ggctactcct catgttgcag gtgcggccgc ccttgttaaa 1020
caaaagaacc catcttggtc taatgtacgt attcgaaatc atctaaagaa tacggcaact 1080
agtttaggaa gcacggactt gtatggaagc ggacttgtta acgcagaagc ggcaacgcgt 1140
taa 1143

<210> SEQ ID NO 16
<211> LENGTH: 269
<212> TYPE: PRT
<213> ORGANISM: Artificial
<220> FEATURE:
<223> OTHER INFORMATION: Polypeptide 16

<400> SEQUENCE: 16

Ala Gln Val Val Pro Trp Gly Ile Ser Arg Val Gln Ala Pro Thr Ala
1 5 10 15

His Asn Arg Gly Leu Thr Gly Ser Gly Val Lys Val Ala Val Leu Asp
20 25 30

Thr Gly Ile Ser Thr His Pro Asp Leu Asn Ile Arg Gly Gly Ala Ser
35 40 45

Phe Val Pro Gly Glu Pro Ser Thr Gln Asp Gly Asn Gly His Gly Thr
50 55 60

His Ala Ala Gly Thr Ile Ala Ala Leu Asn Asn Ser Ile Gly Val Leu
65 70 75 80

Gly Val Ala Pro Ser Ala Glu Leu Tyr Ala Val Lys Val Leu Gly Ala
85 90 95

-continued

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Pro Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Arg Ile
225                 230                 235                 240

Arg Asn His Leu Lys Asn Thr Ala Thr Ser Leu Gly Ser Thr Asp Leu
                245                 250                 255

Tyr Gly Ser Gly Leu Val Asn Ala Glu Ala Ala Thr Arg
            260                 265

<210> SEQ ID NO 17
<211> LENGTH: 1143
<212> TYPE: DNA
<213> ORGANISM: Artificial
<220> FEATURE:
<223> OTHER INFORMATION: Artificial DNA 17

<400> SEQUENCE: 17
atgaaaaaac cgctggggaa aattgtcgca agcaccgcac tactcatttc tgttgctttt 60
agttcatcga tcgcatcggc tgctgaagaa gcaaaagaaa aatatttaat tggctttaat 120
gagcaggaag ctgtcagtga gtttgtagaa caagtagagg caaatgacga ggtcgccatt 180
ctctctgagg aagaggaagt cgaaattgaa ttgcttcatg aatttgaaac gattcctgtt 240
ttatccgttg agttaagccc agaagatgtg gacgcgcttg aactcgatcc agcgatttct 300
tatattgaag aggatgcaga agtaacgaca atggcgcaag ttgtaccatg gggaattcgc 360
cgtgtgcaag ccccagctgc ccataaccgt ggattgacag gttctggtgt aaaagttgct 420
gtcctcgata cagggatatc cactcatcca gatctagata ttcgtggtgg cgcaagcttt 480
gtaccagggg aaccgtcgac tcaagatggg aatgggcatg gcacgcatgc ggccgggacg 540
atcgctgctt taaacaattc gattggcgtt cttggcgtag ctcctagcgc tgagctatac 600
gctgttaaag tcctaggagc aagcggttca ggttcggtca gctcgattgc ccaaggattg 660
gaatgggcag ggaacaatgg catgcacgtt gctaatttga gtttaggaag cccttcgcca 720
agtgccacac tcgagcaagc tgttaatagc gcgacttcta gaggcgttct tgttgtagcg 780
gcatctggga attcaggtgc aggctcaatc agctatccgg cgcgctatgc gaacgcaatg 840
gcagtcggag ctactgatca aaacaacaac cgcgctagct tttcacagta tggcccaggc 900
cttgacattg tcgcacccgg ggtaaacgtg cagagcacat acccaggttc aacatatgcc 960
agcttgaacg gtacatcgat ggctactcct catgttgcag gtgcggccgc ccttgttaaa 1020
caaaagaacc catcttggtc taatgtacgt attcgaaatc atctaaagaa tacggcaact 1080

```
agtttaggaa gcacggactt gtatggaagc ggacttgtta acgcagaagc ggcaacgcgt   1140

taa                                                                 1143


<210> SEQ ID NO 18
<211> LENGTH: 269
<212> TYPE: PRT
<213> ORGANISM: Artificial
<220> FEATURE:
<223> OTHER INFORMATION: Polypeptide 18

<400> SEQUENCE: 18

Ala Gln Val Val Pro Trp Gly Ile Arg Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asp Ile Arg Gly Gly Ala Ser
        35                  40                  45

Phe Val Pro Gly Glu Pro Ser Thr Gln Asp Gly Asn Gly His Gly Thr
    50                  55                  60

His Ala Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Pro Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Arg Ile
225                 230                 235                 240

Arg Asn His Leu Lys Asn Thr Ala Thr Ser Leu Gly Ser Thr Asp Leu
                245                 250                 255

Tyr Gly Ser Gly Leu Val Asn Ala Glu Ala Ala Thr Arg
            260                 265


<210> SEQ ID NO 19
<211> LENGTH: 269
<212> TYPE: PRT
<213> ORGANISM: Bacillus Lentus

<400> SEQUENCE: 19

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30
```

-continued

```
Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```